United States Patent [19]
Uejima et al.

[11] Patent Number: 5,902,105
[45] Date of Patent: May 11, 1999

[54] DENTAL TREATMENT APPARATUS WITH A ROOT CANAL LENGTH MEASUREMENT FUNCTION

[75] Inventors: Yoshio Uejima; Kazunari Matoba; Masanobu Yoshida; Masaru Okumura; Ryozo Koyama, all of Kyoto, Japan

[73] Assignee: Kabushiki Kaisha Morita Seisakusho, Kyoto, Japan

[21] Appl. No.: 08/916,597

[22] Filed: Aug. 22, 1997

Related U.S. Application Data

[63] Continuation of application No. 08/454,640, May 31, 1995, abandoned.

[30] Foreign Application Priority Data

Jun. 9, 1994 [JP] Japan .................................. 6-152938
Jun. 23, 1994 [JP] Japan .................................. 6-164552

[51] Int. Cl.⁶ .................................................. A61C 1/00
[52] U.S. Cl. .................................. 433/27; 433/77; 433/98
[58] Field of Search ............................... 433/27, 72, 75, 433/77, 98

[56] References Cited

U.S. PATENT DOCUMENTS

| | | | |
|---|---|---|---|
| 4,193,408 | 3/1980 | Fujino | 433/27 |
| 4,501,555 | 2/1985 | Ditchburn | 433/29 |
| 4,622,503 | 11/1986 | Sundblom et al. | 433/27 |
| 5,139,421 | 8/1992 | Verderber | 433/30 |
| 5,145,369 | 9/1992 | Lustig et al. | 433/118 |
| 5,295,833 | 3/1994 | Chihiro et al. | 433/224 |
| 5,453,008 | 9/1995 | Berlin | 433/122 |

*Primary Examiner*—John Hilten
*Attorney, Agent, or Firm*—Koda & Androlia

[57] ABSTRACT

A dental treatment apparatus with a root canal length measurement function comprising a cordless handpiece equipped with at least a cutting tool drive motor, a root canal length measurement circuit and a power supply battery, and a charger equipped with at least a charge circuit for charging the power supply battery. With this structure, the handpiece can be operated as desired without interference with any tube since no tube is necessary to connect the handpiece to a main control unit, thereby capable of providing an easy-to-use treatment apparatus. By charging the power supply battery for the handpiece using the charger, the battery can be used repeatedly.

20 Claims, 17 Drawing Sheets

DENTAL TREATMENT APPARATUS WITH A ROOT CANAL LENGTH MEASUREMENT FUNCTION

This application is a continuation of application Ser. No. 08/454,640, filed May 31, 1995, now abandoned.

BACKGROUND OF THE INVENTION

1. Field of the Invention

The present invention relates to improvements in a dental treatment apparatus with a root canal length measurement function, being capable of treating root canals while measuring the lengths thereof by using a cutting tool also as an electrode for root canal length measurement.

2. Description of the Prior Art

Apparatuses being capable of treating root canals while measuring the lengths thereof by using a cutting tool, such as a file or a reamer, also as an electrode for root canal length measurement are known. (Refer to Japanese Utility Model Publication No. 57-3303 and Japanese Laid-open Patent Application No. 5-64643, for example.) The handpiece used in this case is connected to the main control unit via a single tube in which control lead wires and other wires and pipes, such as a water supply pipe when required, are incorporated. This tube forms a cause for worsening the operability of the handpiece. Furthermore, since in a conventional apparatus, a root canal length measurement circuit and an indication section for showing the measurement results are installed in the main control unit which is separate from the handpiece, the operator of the apparatus is required to turn his eyes from an affected part to the indication section each time confirming the indicated data.

In the above-mentioned conventional example, the lead wires for the root canal length measurement circuit are directly connected from the main control unit to the cutting tool of the handpiece, separately from the above-mentioned tube. This structure worsens the operability of the handpiece, and requires to externally connect the lead wires of the measurement circuit at each treatment, making operation troublesome.

SUMMARY OF THE INVENTION

The present invention is intended to solve these problems. The first object of the present invention is to improve the operability of a treatment apparatus equipped with a root canal length measurement function by using a cordless handpiece. The second object is to provide a cordless handpiece to be used for the above-mentioned apparatus. Furthermore, the third object is to improve the operability of a conventional apparatus wherein a tube is used to connect the handpiece to the main control unit. Moreover, the fourth object is to provide the head for the above-mentioned handpiece, which is installed at the tip of the handpiece and used for treatment.

To accomplish the above-mentioned objects, the dental treatment apparatus with the root canal length measurement function of the present invention comprises a cordless handpiece equipped with at least a cutting tool drive motor, a root canal length measurement circuit and a power supply battery, and a charger equipped with at least a charge circuit for charging the above-mentioned power supply battery. This structure can provide an easy-to-use treatment apparatus wherein the handpiece can be used as desired, since no concern is required for the tube which is used in the conventional apparatus to make a connection between the handpiece and the main control unit. The power supply battery of the handpiece can be charged by the charger when required.

In addition, the cordless handpiece of the present invention comprises a main unit equipped with at least a cutting tool drive motor, a root canal length measurement circuit and a power supply battery, and a head equipped with a cutting tool which is also used for root canal length measurement.

The dental treatment apparatus with a root canal length measurement function, wherein a tube is used to make a connection between the handpiece and the main control unit, has a drive control means which automatically stops or reversely rotates the cutting tool or reduces the operating speed of the cutting tool when the insertion of the cutting tool into a setting position in a root canal is detected by root canal measurement. With this means, the operability of the conventional apparatus can be improved. Hereinafter, the control used to automatically stop or reversely rotate the cutting tool or reduce the operating speed of the cutting tool when the cutting tool is inserted into a setting position is generally referred to as "auto-stop."

Furthermore, in the present invention, the handpiece head installed at the tip of the handpiece and used for dental treatment has a structure wherein the portion to be mounted on the main unit of the handpiece is electrically connected to a tool holding mechanism for holding the cutting tool through an electrically conductive members in the head. Or the head has a structure wherein the portion to be mounted on the main unit of the handpiece is electrically connected to the cutting tool through a contact piece which makes contact with the cutting tool installed in the tool holding mechanism. Accordingly, the cutting tool installed in the tool holding mechanism establish conduction to one side of the root canal length measurement circuit through the internal conductive member or the external contact piece. This eliminates the need for externally connecting the lead wires for the measurement circuit to the head of the handpiece.

The above descriptions refer to the basic structures of the apparatus of the present invention. More specific structures will be made apparent by the descriptions regarding the following embodiments.

DETAILED DESCRIPTION OF THE PREFERRED EMBODIMENTS

Figure 1:
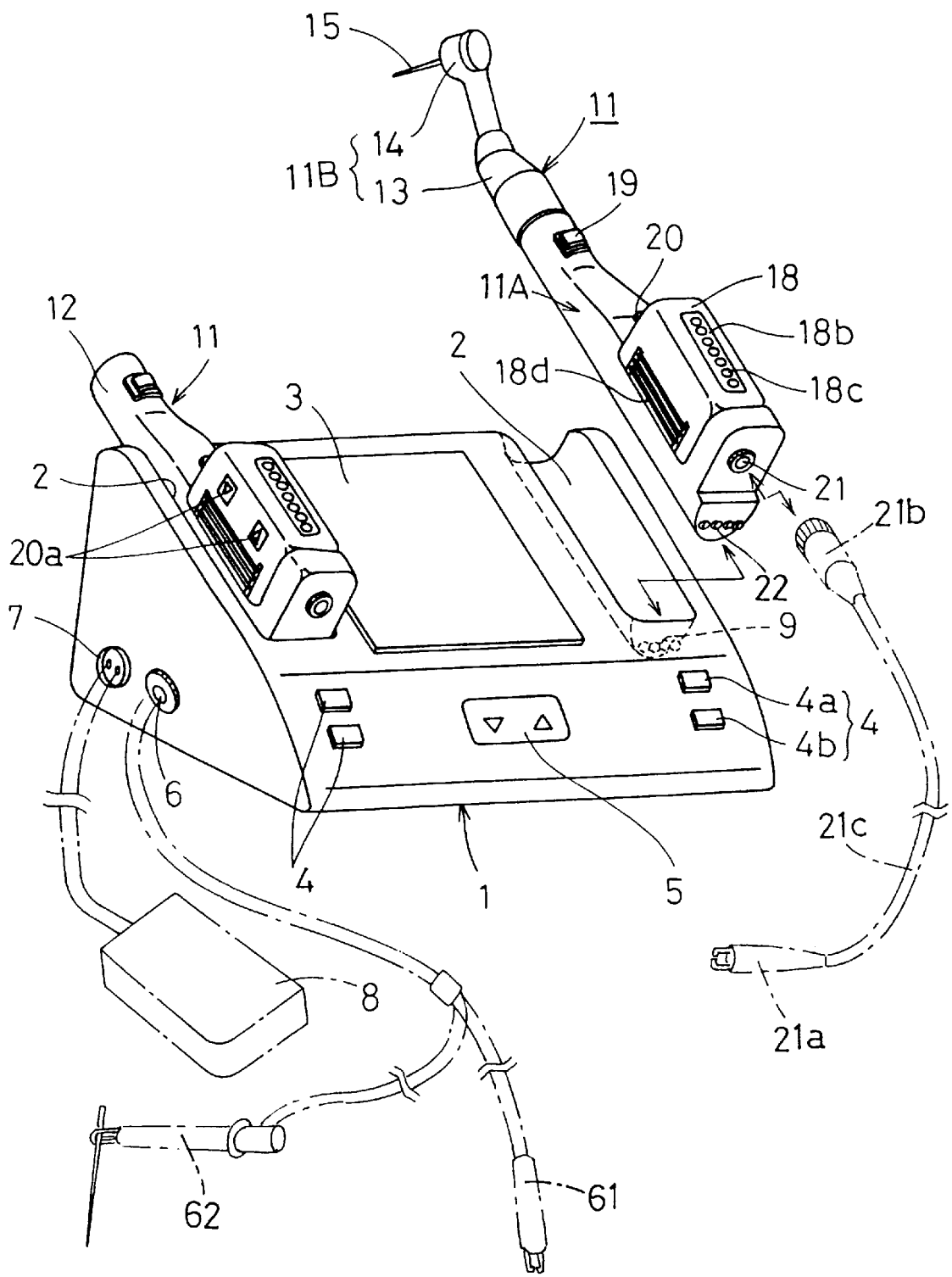
FIG. 1 is an external perspective view of an embodiment of an entire apparatus of the present invention.
Figure 2:
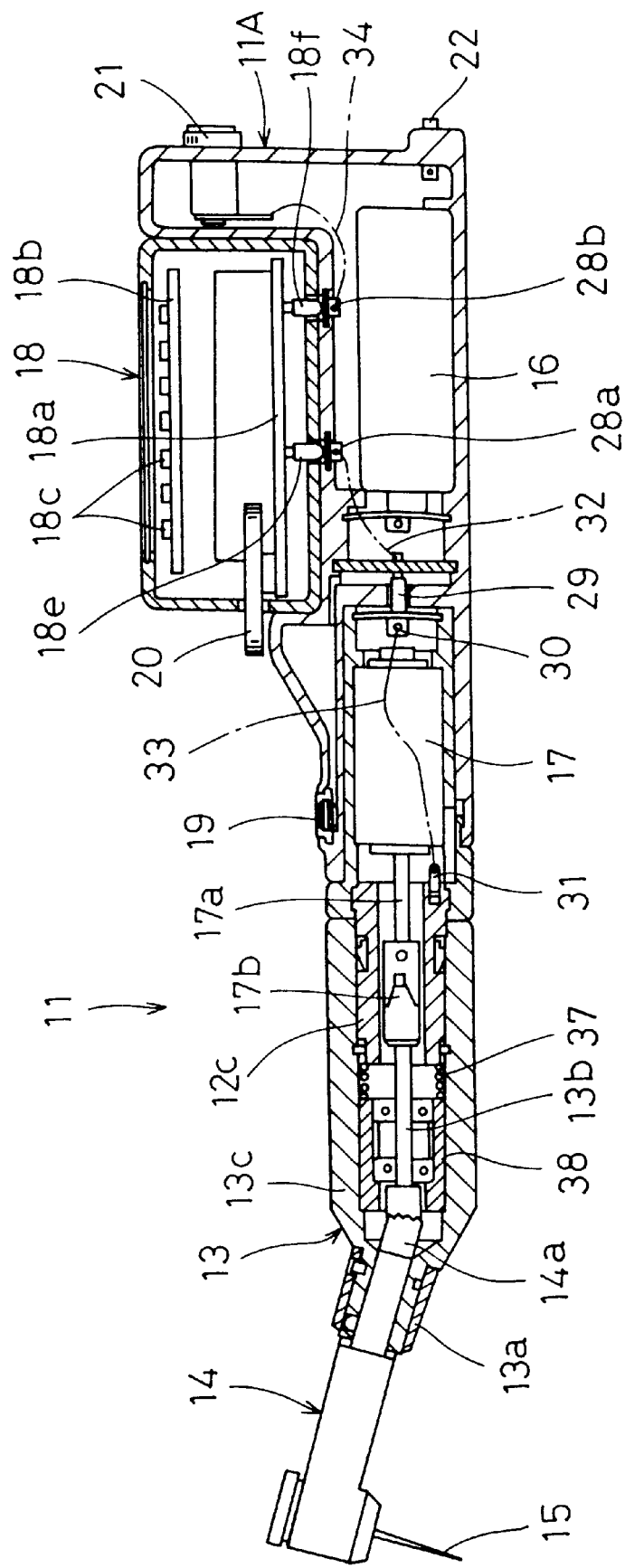
FIG. 2 is a transverse sectional view of the handpiece of the embodiment.
Figure 3:
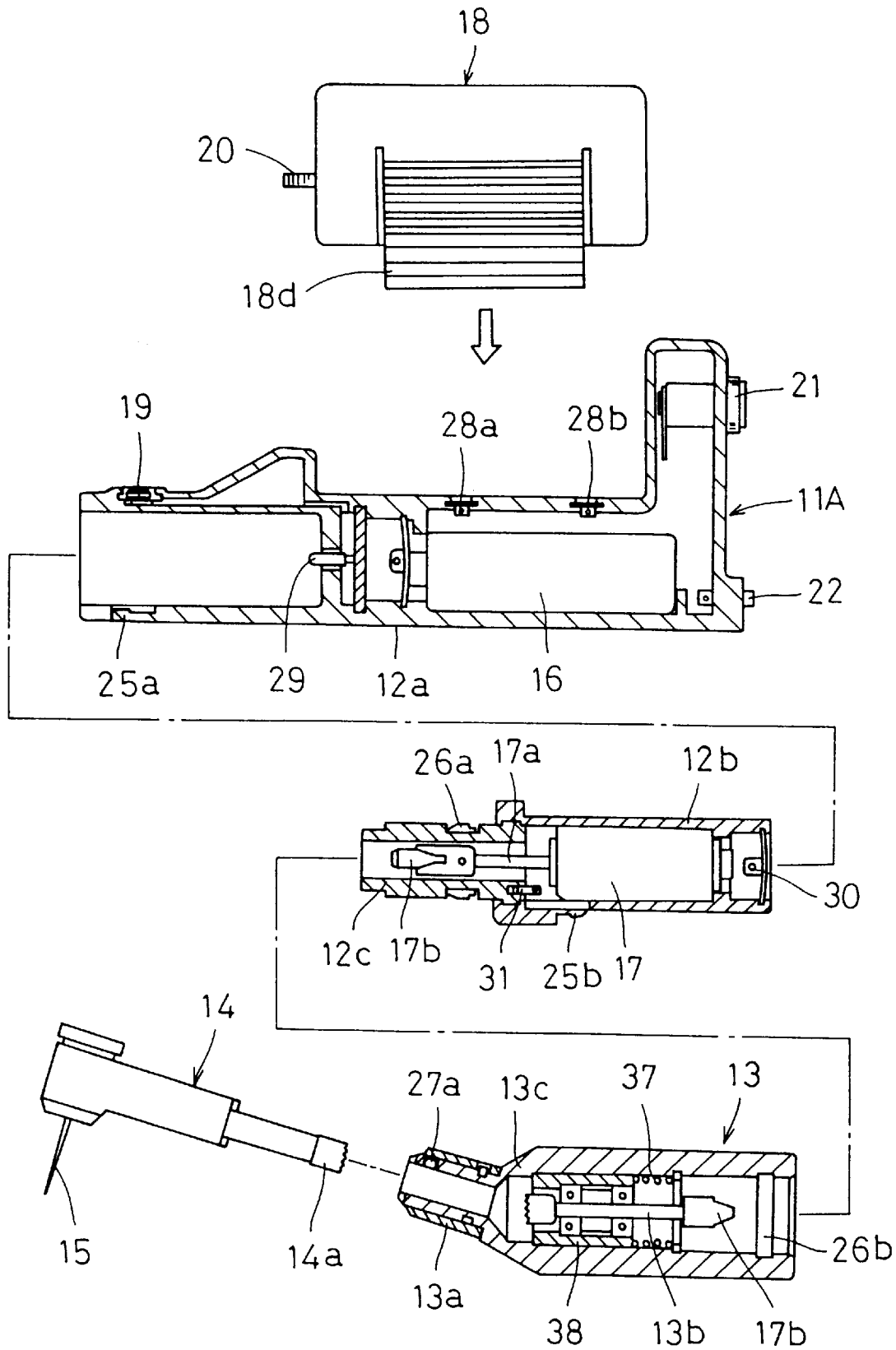
FIG. 3 is an exploded sectional view of the handpiece of the embodiment.

First, an embodiment of an apparatus which uses a cordless handpiece is explained below. Referring to FIG. 1, numeral 1 represents a charger, numeral 2 represents a setting section, numeral 3 represents an indication section, numeral 4 represents a charge indication lamp consisting of a charging indication lamp 4a and a charge completion indication lamp 4b, numeral 5 represents a position setting switch used to set an auto-stop position, numeral 6 represents a jack for the root canal length measurement circuit, numeral 7 represents a connector used to externally connect an external unit, numeral 8 represents a foot pedal connected to the connector 7, numeral 9 represents a connector used to connect the handpiece. The setting section 2 is formed in a groove shape on the upper surface of the charger 1 to accommodate the main unit of the handpiece described later. The connector 9 used to connect the handpiece is provided at the end of the internal surface of the setting section 2. Numeral 11 represents a handpiece. As shown in FIGS. 2 and 3, a head unit 11B is installed at the tip of the main unit 11A. The main unit 11A comprises a battery module 12a and a motor module 12b. The head unit 11B comprises a shank module 13 and a head 14. The head 14 is installed in the main unit 11A via the shank module 13. The head 14 is structured to accommodate a cutting tool 15, such as a file, a reamer or a drill. In addition, a power supply battery 16 is built in the battery module 12a, and a motor 17 is built in the motor module 12b. A root canal length measurement module 18 equipped with a control circuit board 18a and an indication board 18b is externally connected to the battery module 12a, and the indication board 18b has a plurality of LEDs 18c arranged in a row.

The above-mentioned root canal length measurement module 18 is mechanically fixed to the main unit 11A by a pair of engagement pieces 18d (right and left pieces) and electrically connected to the main unit 11A by terminals 18e and 18f. In addition to the control of root canal length measurement, the control circuit board 18a operates as the control unit for the entire handpiece by controlling the operation of the motor 17 and the communication with the charger 1 as described later, for example. Numeral 19 represents a main switch and numeral 20 represents a speed controller. The main switch 19 is installed close to the upper surface of the tip of the battery module 12a. The speed controller 20 is installed in the root canal length measurement module 18 with the outer circumference of the knob thereof exposed partially. Furthermore, at the end surface on the hand grip side of the main unit 11A, a root canal length measurement jack 21 to be connected to the ground electrode for root canal measurement and a connector 22 to be connected to the charger 1 are provided. This connector 22 and the connector 9 of the charger 1 are connected to each other when the handpiece 11 is properly set in the setting section 2 as shown in FIG. 1.

The above-mentioned main switch 19 is used to simultaneously turn on and off the motor 17 and root canal length measurement. The speed controller 20 is used to adjust the variable resistor provided on the control circuit board 18a to set the rotation speed of the motor 17 and the auto-stop position for root canal length measurement. To accomplish these purposes, a momentary switch is used as the main switch 19 so that the switch can be turned on when pushed and turned off when released. This main switch is used in combination with a control circuit consisting of a relay or the like so that the push operation can be latched, whereby the two functions: the ON/OFF function of the motor and root canal length measurement and the ON/OFF function of auto-stop can be selectively used by a single switch in accordance with the length of the push operation time. In other words, when the main switch 19 is pushed for a short time and released, the motor 17 is rotated and root canal length measurement is turned on with auto-stop being ready to activate. When the switch 19 is operated again, the motor 17 is stopped and root canal length measurement is turned off simultaneously. When the main switch 19 is kept pushed, the motor 17 rotates and root canal length measurement is turned on with the auto-stop function released. In the condition that this main switch 19 is kept pushed, the auto-stop position can be set by the speed controller 20. In this way, by selectively using the main switch 19 in accordance with the length of the push operation time and by assigning the auto-stop position setting function to both the switch 19 and the speed controller 20, the appearance of the handpiece 11 can be made simple.

Instead of this kind of selective usage, a dedicated auto-stop position setting switch can be installed on the handpiece 11 so that when the setting position is changed by operation the position can be memorized and the indication can also be changed. Referring to FIG. 1, numeral 20a represents a position setting switch equipped with an UP or DOWN operation section. FIG. 1 shows an example wherein this switch 20a is installed only on the left main unit 11A. With this structure, operation is made slightly simpler than the case of the above-mentioned selective usage. This structure can thus be regarded suitable when attaching importance to operability.

The battery module 12a and the motor module 12b, the motor module 12b and the shank module 13, and the shank module 13 and the head 14 have connectable and disconnectable structures to allow insertion and removal. More specifically, the battery module 12a and the motor module 12b are securely held by the engagement of the engagement sections 25a and 25b. The motor module 12b and the shank module 13 are also securely held by the engagement of the spring ring 26a and the ring groove 26b. The motor module 12b is ratatably connectable to and disconnectable from the shank module 13. Furthermore, the shank module 13 and the head 14, which constitute the head unit 11B, are securely held and unrotatably fixed by a ball 27a which is exposed to the internal surface by rotating the ring member 13a having an eccentric groove on the internal circumference surface thereof, and by engaging the ball 27a with the hole 27b disposed in the head shown in FIG. 4. This engagement can be released when required. The above-mentioned secure holding structures can have appropriate structures other than those shown in the figures.

In the connection conditions of the modules, the motor 17 is driven by the power supply battery 16 and controlled by the control circuit board 18a of the root canal length measurement module 18. The rotation of the output shaft 17a of the motor 17 is transmitted to the rotation shaft 13b via a clutch 17b and further transmitted to the drive gear 14a of the head 14.

Figure 4:
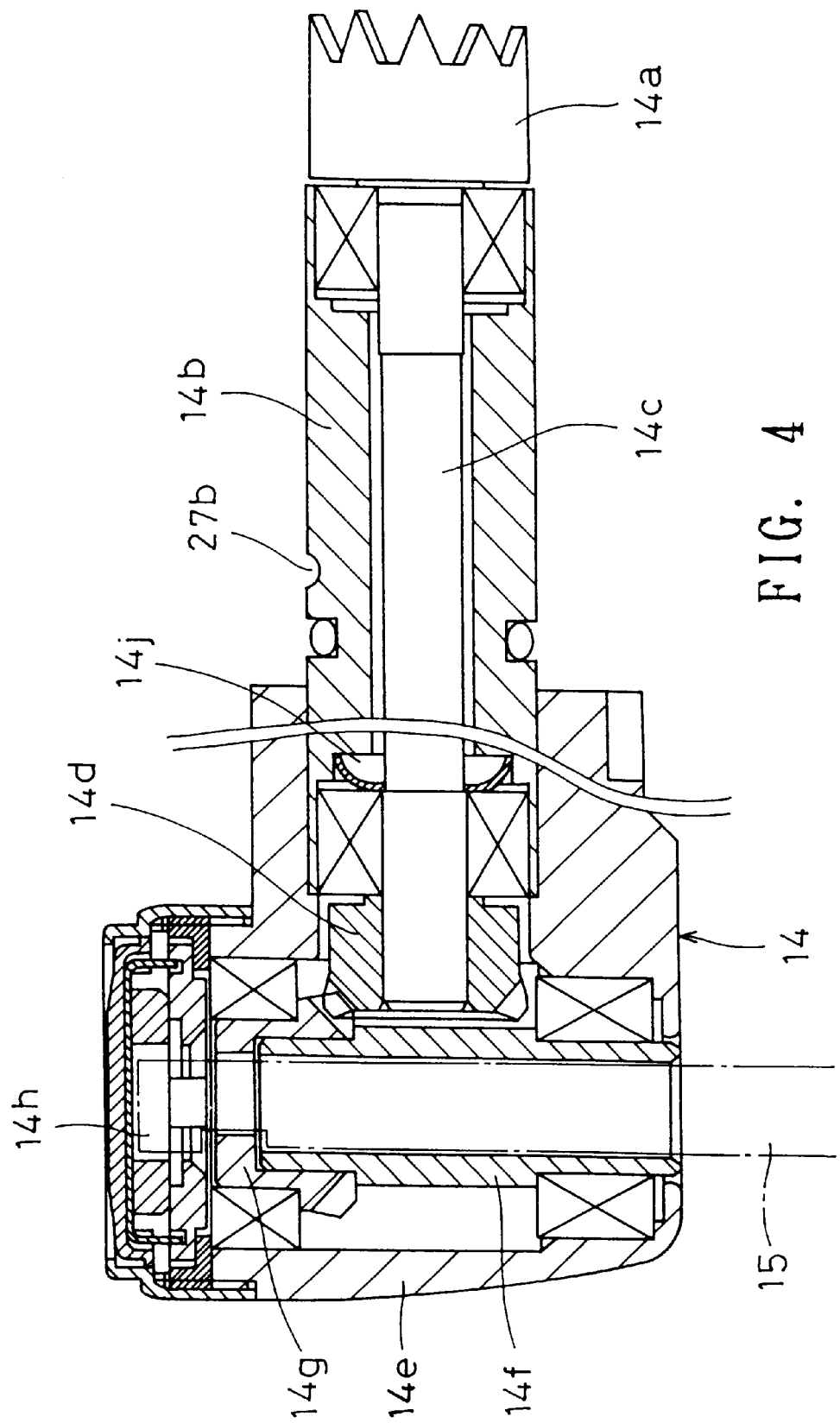
FIG. 4 is a sectional view of the head of the embodiment.

The head 14 has a structure shown in FIG. 4. The drive gear 14a is installed at one end of a rotation shaft 14c supported by a bearing holder 14b. At the other end, a front gear 14d is installed. This front gear 14d is engaged with a rotor gear 14g installed on a rotation shaft 14f supported by a head housing 14e. At the upper end of the rotation shaft 14f, a tool holding mechanism 14h is installed. The above-mentioned basic structure is similar to that known conventionally. A known mechanism can thus be used as the tool holding mechanism 14h. A cutting tool 15 being held by this mechanism rotates in accordance with the rotation of the drive gear 14a. In this embodiment, however, the following structures is added. That is to say, numeral 14j represents a wave washer made of a spring material and the washer is inserted between the bearing holder 14b and the bearing of the rotation shaft 14c. As a result, the rotation shaft 14c is pushed in the left direction in FIG. 4. By the pushing force, the front gear 14d is pressed against the rotor gear 14g so that both the gears 14d and 14g can make reliable contact with each other even during rotation. Furthermore, all members relating to the mechanism ranging from the bearing holder 14b to the wave washer 14j, the rotation shaft 14c, the bearing of the rotation shaft 14c, the gears 14d and 14g, and the tool holding mechanism 14h are made of metallic materials or other electrically conductive materials so that electrical conduction can be established between the bearing holder 14b and the tool holder mechanism 14h. Instead of the wave washer 14j, an elastic member, such as a spring (a coil spring or a belleville spring) or an electrically conductive rubber piece, can also be used.

The terminal 18e of the root canal length measurement module 18 is a terminal for one of the electrodes of the measurement circuit. A lead wire 32 shown by a chain line in FIG. 2 is connected between the terminal 28a (connected to the terminal 18e) and the connector pin 29 of the battery module 12a. A lead wire 33 shown by another chain line in FIG. 2 is also connected between the terminal 30 (connected to the connector pin 29) and the terminal 31 of the motor module 12b. Furthermore, the end surface of the insertion section 12c equipped with the terminal 31 in the motor module 12b makes pressure contact with an electrically conductive spring 37 in the shank module 13, is rotatably connectable to and disconnectable from the shank module 13 by the engagement between an electrically conductive spring 26a and a ring groove 26b, and is made electrically conductive to the bearing holder 14b of the head module 14 via the spring 37, the bearing member 38 and the housing 13c of the shank module 13. With this structure, the motor module 12b is connectable and disconnectable, and rotatable while electrical conduction is maintained between the motor module 12b and the shank module 13. In this structure, all members relating to the insertion section 12c, the spring 37, the bearing member 38 and the housing 13c are made of metallic materials or other electrically conductive materials.

A lead wire 34 shown by a still another chain line in FIG. 2 is connected between a terminal 28b (connected to the other terminal 18f of the root canal length measurement module 18) and the jack 21 for root canal length measurement. The connection of the connector 22 is not shown. The connector is explained referring to the block diagram in FIG. 6.

With the above-mentioned structure, the terminal 18e of the root canal length measurement module 18 is made electrically conductive to the cutting tool 15 installed in the head 14 via electrically conductive materials in the handpiece 11. As a result, no external wiring is necessary for the cutting tool 15. Root canal length measurement can be performed simply by connecting the ground electrode 21a (receptacle electrode) to the jack 21 for root canal length measurement via a lead wire 21c equipped with a connector 21b. The handpiece 11 can thus be operated without interfering with any external wires to the cutting tool 15. As a result, the handpiece can have remarkably improved operability and can eliminate the inconvenience of connecting external wires at each treatment.

In order to form such a conduction circuit described above in the head unit 11B comprising the head 14 and the shank module 13, all members related to the circuit are made of electrically conductive materials. The surface of the housing 13c of the shank module 13 is provided with an insulating film. The housing 14e of the head 14 can be made of an insulating material such as a synthetic resin, since the housing is not included in any part of the above-mentioned conduction circuit. However, when the housing is made of an electrically conductive material, the surface thereof is provided with an insulating film in the same way as the housing 13c of the shank module 13. These insulating films are not shown in the figure since they are very thin. As describe above, in the embodiment, the head 14 and the shank module 13 are the members having insulating surfaces. However, this is just an example. At least a portion of the handpiece 11 which might be inserted into the mouth of a patient should be insulated in accordance with the entire shape and structure of the handpiece 11. By this insulation, even if the handpiece 11 makes contact with the tissues in the mouth or the like of the patient during root canal length measurement, the measurement circuit is not affected adversely and it is possible to continue measurement without problems.

Figure 5:
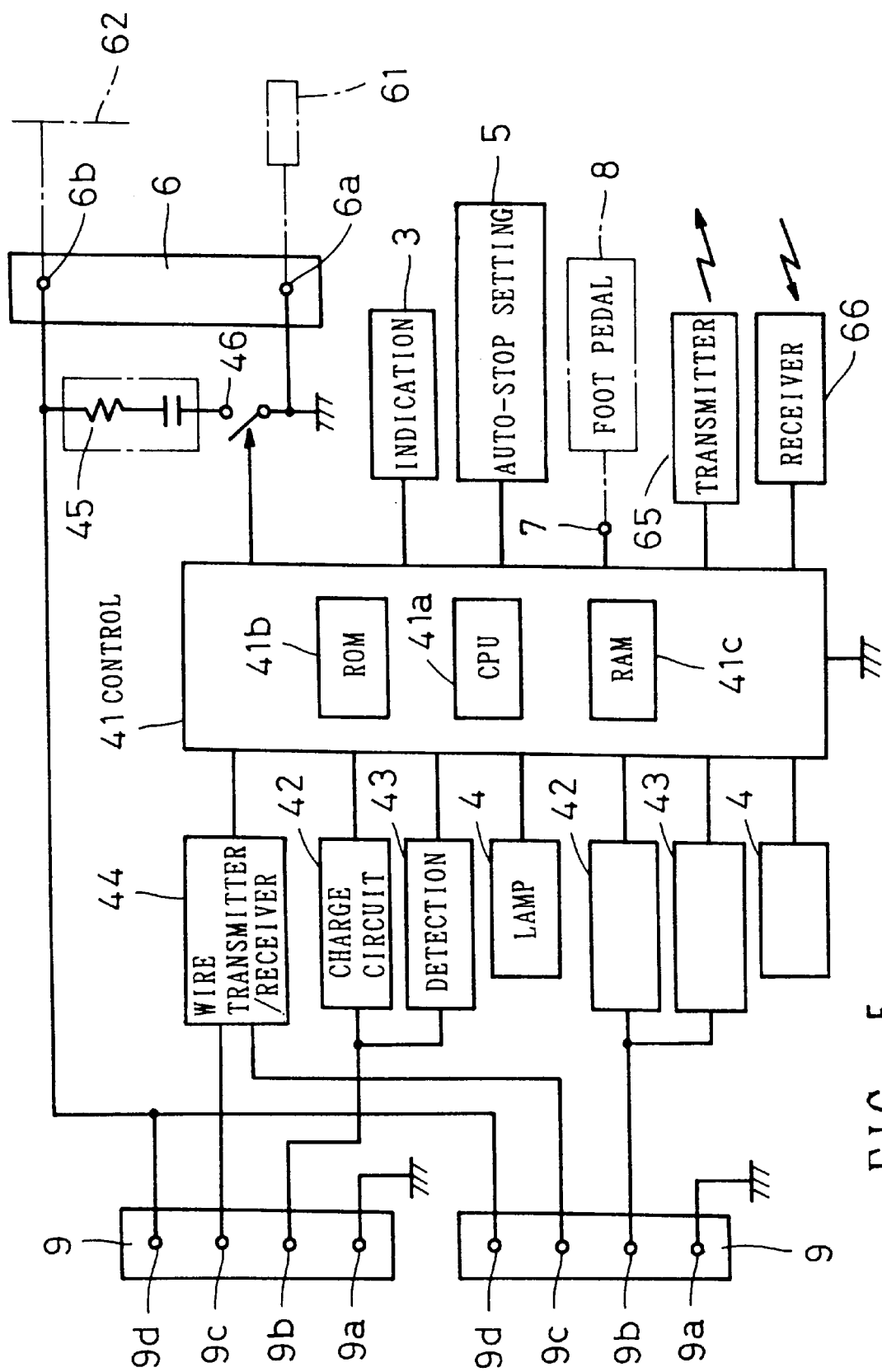
FIG. 5 is a block diagram of the control circuit of the charger of the embodiment.
Figure 6:
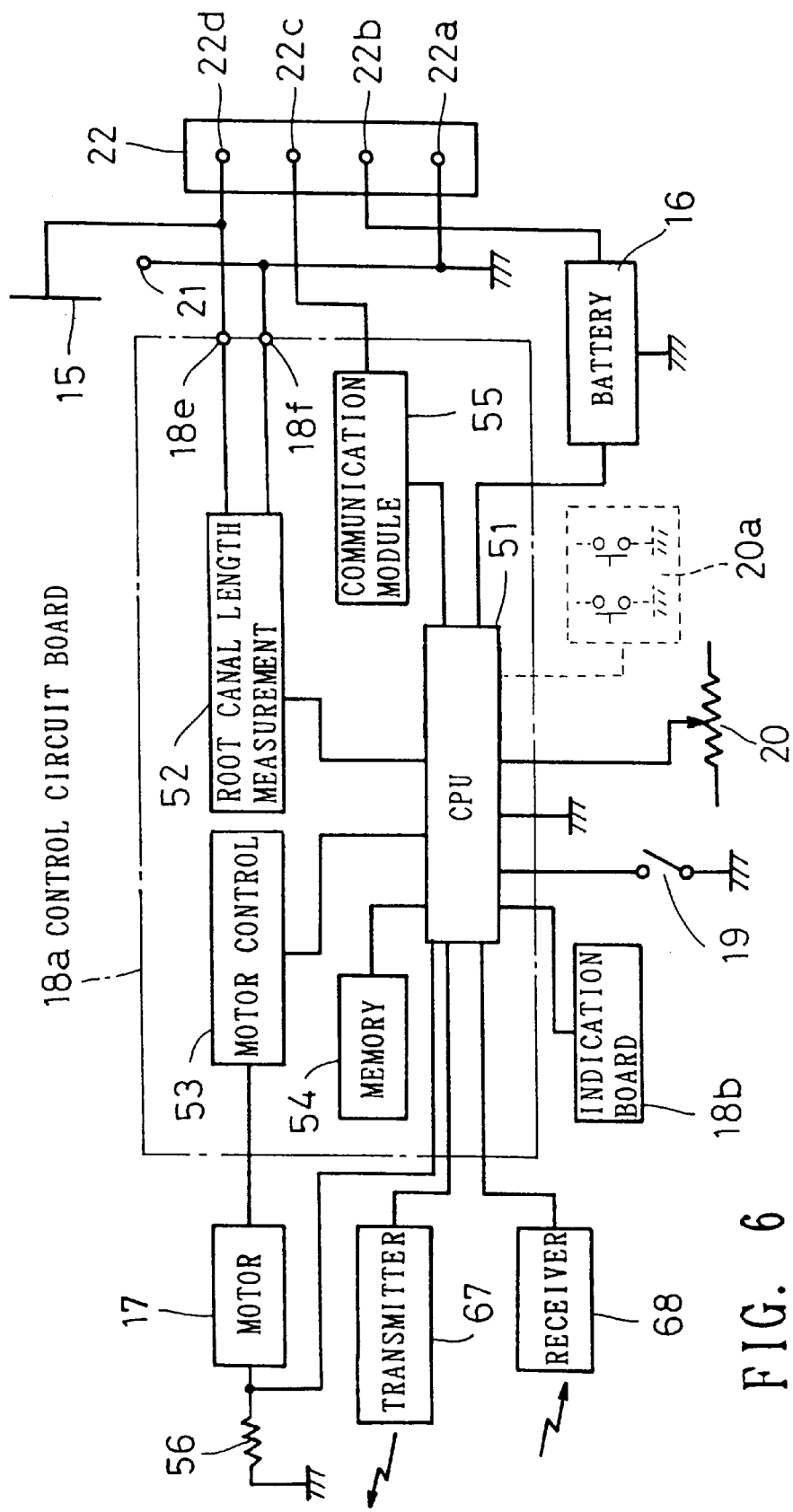
FIG. 6 is a block diagram of the control circuit of the handpiece of the embodiment.

Next, the control circuit is explained referring to the block diagrams in FIGS. 5 and 6. FIG. 5 shows the circuit of the charger and FIG. 6 shows the circuit of the handpiece. In FIG. 5, numeral 41 represents a control section equipped with a CPU 41a for arithmetic operation, a ROM 41b and a RAM 41c for control and storage, and input/output ports (not shown). Numeral 42 represents a charge circuit, numeral 43 represents a voltage detection circuit and numeral 44 represents a wire transmitter/receiver. As shown in FIG. 5, these are connected to the control section 41 together with the indication section 3, the indication lamp 4, the auto-stop position setting switch 5, the connectors 7 and 9, etc. shown in FIG. 1.

The connector 9 has 4 terminals; numeral 9a represents a ground terminal, numeral 9b represents a charge terminal, numeral 9c represents a transmitting/receiving terminal, and numeral 9d represents a terminal for the root canal length measurement circuit. Between the terminal 9d for the root canal length measurement circuit and the ground, a series circuit comprising an equivalent impedance 45 for calibration and a calibration switch 46, and the jack 6 for the root canal length measurement circuit are connected. The calibration switch 46 is controlled by the control section 41. The commercially available power supply circuit for the charger 1 is not shown.

In FIG. 6, numeral 51 represents a CPU, numeral 52 represents a root canal length measurement circuit, numeral 53 represents a motor control section, numeral 54 represents a memory, numeral 55 represents a communication module, and numeral 56 represents a motor current detection resistor. These components constitute the control circuit board 18a. To this control circuit board 18a, the cutting tool 15, the power supply battery 16, the motor 17, the indication board 18b, the main switch 19, the speed controller 20, the jack 21 for connecting the ground electrode for root canal length measurement and the connector 22 are connected. When the auto-stop position setting switch 20a is installed, this switch is also connected as shown by broken lines. For the memory 54, an EEPROM is used for example. The connector 22 has 4 terminals corresponding to the terminals of the connector 9 of the charger 1. Numeral 22a represents a ground terminal, numeral 22b represents a charge terminal, numeral 22c represents a transmitting/receiving terminal and numeral 22d represents a terminal for the root canal length measurement circuit. The plus terminal of the power supply battery 16 is connected to the charge terminal 22b, the terminal 18e of the root canal length measurement circuit 52 is connected to the terminal 22d, and the communication module 55 is connected to the transmitting/receiving terminal 22c. When the handpiece 11 is set in the charger 1, these terminals are connected to the corresponding terminals of the connector 9.

The configurations of the circuits are described above. When the handpiece 11 is set in the setting section 2 of the charger 1 and the connector 22 is connected to the connector 9, the power supply battery 16 is charged by the charge circuit 42 under the control of the control section 41. When the voltage detection circuit 43 detects that a predetermined terminal voltage value is reached, charge is stopped. The jack 6 for the root canal length measurement circuit is a measurement terminal which conducts to the root canal length measurement circuit 52 of the handpiece 11 while the handpiece 11 is set in the charger 1. Accordingly, when a ground electrode 61 is connected to the ground terminal 6a, and a measurement terminal 62 is connected to the measurement terminal 6b as shown by chain lines, the root canal length measurement circuit 52 of the handpiece 11 can be used to perform root canal length measurement. In other words, even when the control section 41 of the charger 1 has no root canal length measurement function, the charger 1 can be used as a root canal length measurement unit of an ordinary desk-top type. In this case, the large indication section 3 of the charger 1 can be used. Unlike the small indication board 18 of the handpiece 11, the indication section 3 can offer much information and easy-to-understand indication.

Although the connection conditions of the ground electrode 61 and the measurement electrode 62 to the jack 6 are also shown by chain lines in FIG. 1, the ground terminal 61 can be directly connected to the jack 21 of the handpiece 11 when the handpiece 11 is set in the charger 1. In this case, the ground electrode 21a should have the same specifications as those of the lead wire 21c which is used to connect the ground electrode 21a to the jack 21 when performing root canal length measurement by using the handpiece 11, except that only the entire length of the lead wire 21c is extended.

The charger 1 has two setting sections 2 so that two handpieces 11 can be charged simultaneously. In other words, the charger 1 is used as a charge stand commonly used for the two handpieces. Three or more setting sections 2 can be installed. In this case, the communication described later and the calibration of the root canal length measurement circuit 52 are conducted for one handpiece at a time under the control of the control section 41. FIG. 1 shows a condition wherein only the main unit 11A of one of the two handpieces 11 is set in the setting section 2. Since the handpiece 11 must be compact and lightweight, the control circuit board 18a of the root canal length measurement module 18 which functions as a controller is made compact, and the indication board 18b is relatively simplified only by arranging a plurality of LEDs 18c. In this embodiment, these control and indication functions are limited to a minimum. For example, the detailed contents of measurement results and the setting values of auto-stop positions are stored in the memory 54 of the control circuit board 18a so that data are transmitted and received via the wire transmitting/receiving section 45, stored in the RAM 41c of the control section 41 and indicated on the indication section 3 when the handpiece 11 is set in the charger 1.

It is known that the root canal length measurement circuit must be calibrated to accurately detect that the cutting tool has reached a root apex. In this embodiment, when the handpiece 11 is set in the charger 1, a calibration request signal is output from the CPU 51 of the root canal length measurement module 18 and calibration is performed. The calibration is not required to be performed at each measurement, but should be performed after the number of preset measurement times, 100 times for example. In other words, when the control section 41 receives a calibration request signal, a calibration switch 46 is turned on and the calibration equivalent impedance 45 is connected between the terminal 9d for the root canal length measurement circuit and the ground, then a calibration impedance ON signal is output. On the side of the root canal length measurement module 18, root canal length measurement is performed by such a known calibration method as described in the Japanese Patent Application No. 3-280515 (Japanese Laid-open Patent Application No. 5-92014), for example, applied by the applicants of the present invention, while the signal is output. By using the measurement data, the root canal measurement circuit 52 is calibrated.

Furthermore, in this embodiment, the speed controller 20 of the handpiece 11 can also be used to set the auto-stop position as described already. However, various setting functions, such as the auto-stop position setting function, for controlling the motor 17 can also be provided for the charger 1 so that data transmitted by communication can be stored in the memory 54. The auto-stop position setting switch 5 installed on the charger 1 is intended to set the auto-stop position at the charger 1 and has a function similar to that of the above-mentioned setting switch 20a of the handpiece 11. With this structure, the number of operation members and circuit components mounted on the handpiece 11 can be reduced, thereby being effective in making the handpiece 11 more lightweight. The arrangement of these operation members shown in the figure is only one example. Arrangements other than that shown in the figure can also be used. For example, the speed controller is installed in the charger 1. The operation members of the charger 1 can be provided externally via the connector 7, instead of installing them on the charger 1. The foot pedal 8 shown by chain lines in FIGS. 1 and 5 is shown as an example of operation members to be provided externally. A built-in variable resistor is used to set the speed of the motor 17. In addition, a control switch, which is used when root canal length measurement is performed after the measurement electrode 62 and the ground electrode 61 are connected to the jack 6 for root canal length measurement, or other operation members can be provided on the foot pedal 8. Although the above-mentioned connector 7 is used as an input port from an operation member to be connected externally, an input/output connector being connectable to external apparatuses such as a printer or a computer can be provided so that a system combined with such external apparatuses can be used.

Figure 7:
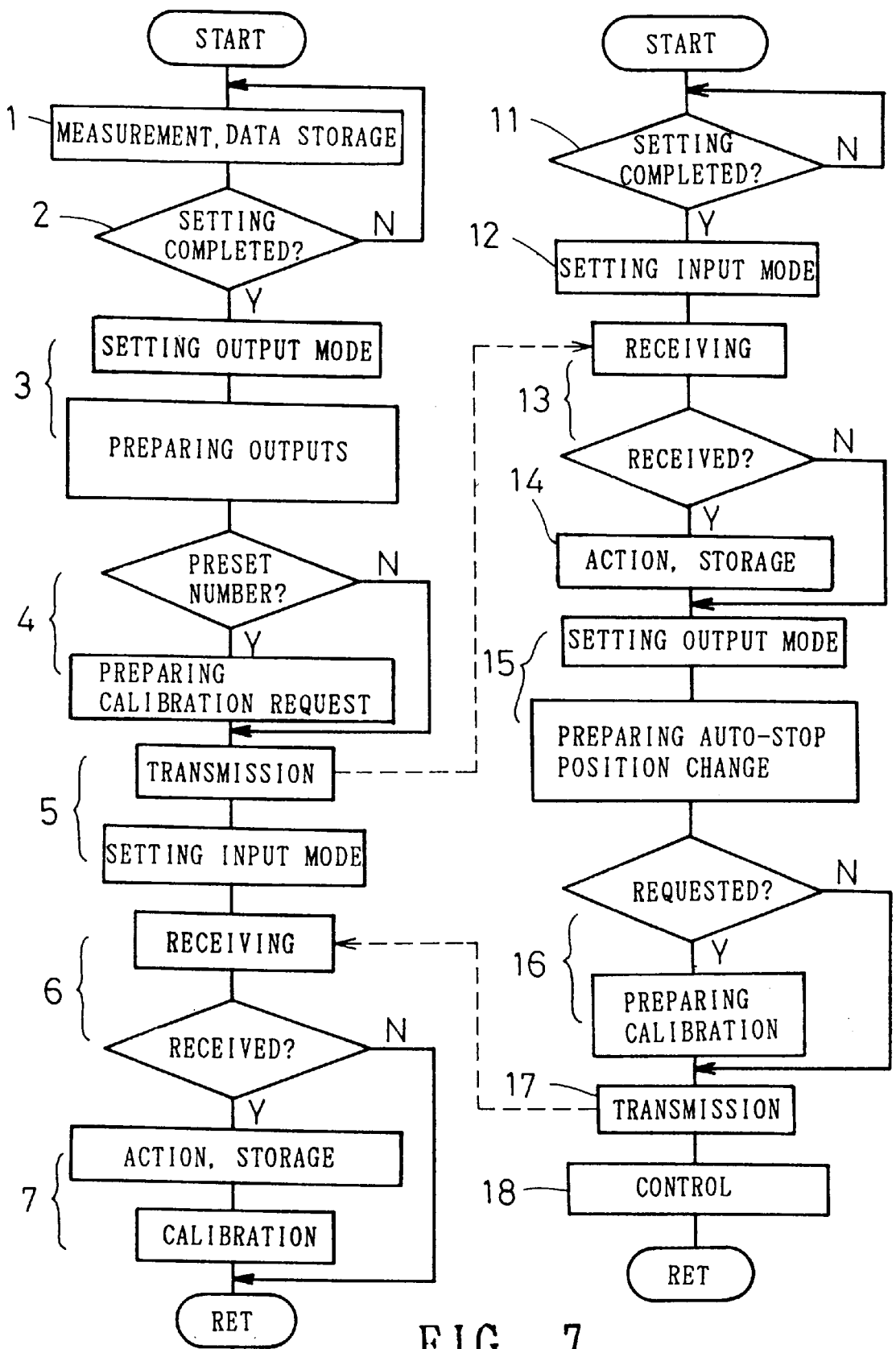
FIG. 7 is a flow chart for the control procedure of the embodiment.

FIG. 7 is a flow chart regarding the basic control procedure mainly concerning the above-mentioned data transmission and reception. The left side of the flow chart indicates the procedure taken by the handpiece 11, and the right side of the flow chart indicates the procedure taken by the charger 1. At step 1 of the procedure taken by the handpiece 11, ordinary root canal length measurement is performed and the results are stored. When the completion of setting is detected at step 2, the procedure goes to step 3. Detecting the completion of setting is done when the CPU 51 of the root canal length measurement circuit 18 detects that the handpiece 11 has been set in the charger 1 and that these two units have been connected electrically. By this detection, mutual communication of data described below can be done with reliability and action can be done without waste. At step 3, the output mode is set, and data output signals for root canal length measurement, auto-stop position, rotation speed, etc. are prepared. At the next step 4, a calibration request signal is prepared when the number of measurements after the previous calibration has reached a preset number. This signal and the signal prepared at step 3 are transmitted to the charger 1 at the next step 5. The input mode is set to make preparation for receiving signals from the charger 1. At step 6, if a signal is transmitted from the charger 1, the signal is received. When the signal is received, the content of the signal is confirmed at the next step 7, and actions, data storage, etc. are done in accordance with the content. When a calibration impedance ON signal is received, calibration is performed. When the signal is not received, no calibration is performed, and the procedure returns to step 1.

On the other hand, when the control section 41 detects that the handpiece 11 has been set in the charger 1, that the two units have been connected electrically, and that the setting has been completed, the procedure goes from step 11 to step 12, and the input mode is set. At the next step 13, if a signal is transmitted from the handpiece 11, the signal is received. When the signal is received, the content of the signal is confirmed at the next step 14, and actions, data indication and storage, etc. are done in accordance with the content. At the next step 15, the output mode is set. When changing the auto-stop position, a signal for the change is prepared. When a calibration request signal is received, the calibration switch 46 is turned on at step 16 and a calibration impedance ON signal is prepared. This signal and the signal prepared at step 15 are transmitted to the handpiece 11 at the next step 17. Charge and other control actions are then performed at step 18.

The above-mentioned sequential actions cannot be performed and no signals are transmitted or received when the completion of setting is not detected at step 1 of the procedure taken by the handpiece 11 or at step 11 of the procedure taken by the charger 1, that is, when the handpiece 11 is not set in the charger 1. Instead of detecting the completion of setting by checking the electrical connection between the handpiece 11 and the charger 1 as described above, a method can be adopted, wherein for example a detection switch, which turns on when pushed by a member located at the position corresponding to the setting position at the time of setting, is provided to detect the completion of setting in accordance with the ON/OFF operation of the switch.

In the above-mentioned description, wire communication is explained, which is performed via the wire transmitting/receiving section 4 when the handpiece 11 has been set in the charger 1. In this embodiment, a wireless communication means is also provided. That is to say, numerals 65 and 66 in FIG. 5 represent wireless transmitting and receiving sections respectively installed in the charger 1. Numerals 67 and 68 in FIG. 6 represent wireless transmitting and receiving sections respectively installed in the handpiece 11. These communication means are configured appropriately to accomplish predetermined communication functions on the basis of known technology using infrared rays, supersonic waves, radio waves, etc. By provided these wireless communication means, when the handpiece 11 is not set in the charger 1, communication can be done and the results of communication can be indicated on the indication panel 3 of the charger 1. As a result, the functions and operability of the treatment apparatus can be improved. In this case, all of data to be transmitted and received by the above-mentioned wire communication means can be handled, since communication is done bidirectionally. However, the circuit configuration for the handpiece 11 is apt to become large and complicated, and the procedure for control is also become complicated. This is not desirable. Therefore, data to be transmitted and received by this wireless communication means should be limited to a certain extent. For example, the data should be limited to those which are specially meaningful clinically when processed in real time, such as root canal length measurement results, auto-stop setting position and the rotation speed of the motor 17, as well as the charge condition (remaining power) of the power supply battery 16. By this limitation, a treatment apparatus with superior functions can be obtained without making the circuit configuration and control procedure for the handpiece 11 complicated. When the control section 41 of the charger 1 detects that the power supply battery 16 is required to be charged soon, this condition should be indicated on the indication section 3 and an alarm should be activated. By incorporating these functions, the handpiece 11 can be prevented from becoming nonoperational due to the discharge of the power supply battery 16 during operation of the handpiece 11 or during root canal length measurement.

In the explanation of the above-mentioned foot pedal 8, a variable resistor is used as an example to set the speed of the motor 17, but the device used to set the speed is not limited to such a variable resistor. When a wireless communication means is provided, the motor can be turned on and off, and the speed of the motor can be adjusted during treatment by foot operation. In addition, the rotation direction of the motor 17 can be changed. With this structure, the cutting tool 15 can be driven as desired, and the motor 17 can be rotated in the reverse direction by operating the foot pedal 8 when the cutting tool 15 reaches a setting position and is stopped automatically. This facilitates root canal forming operation by the cutting tool 15 and removal of the cutting tool from a root canal. Instead of operating the foot pedal 8, the reverse rotation of the motor 17 at the auto-stop position can be activated by operating the main switch 19 of the handpiece 11 for example. Or, the motor can be rotated automatically in the reverse direction for a short time after the tool has reached the auto-stop position and stopped. Furthermore, instead of using lead wires to connect such an operation member as a foot pedal to the charger 1, a wireless communication means can be used to make connection between such an operation member and the charger 1. For example, a wireless transmitting/receiving section which can communicate with the transmitting section 65 and the receiving section 66 of the charger 1 is installed in the foot pedal 8. With this structure, the installation position of the foot pedal 8 can have higher degree of freedom, thereby improving the operability of the foot pedal and eliminating cables which may hinder smooth operation.

Figure 8:
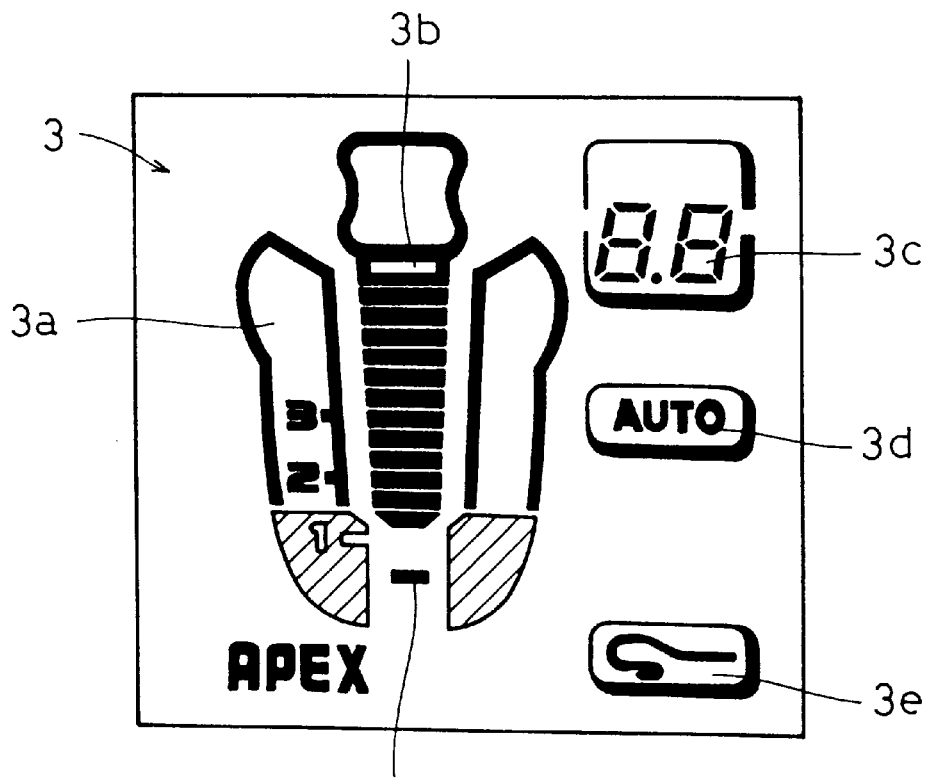
FIG. 8 is a view exemplifying the indication patterns for the charger of the embodiment.

FIG. 8 shows an example of an indication pattern for the indication section 3 of the charger 1. The indication panel 3 is composed of a liquid crystal panel for example. The panel has a tooth indication section 3*a* which shows a tooth, a tool indication section 3*b* equipped with a series of indication dots which are lit in the up-to-down order in accordance with the insertion position of the cutting tool 15, a rotation speed indication section 3*c* which indicates a number corresponding to the rotation speed of the motor 17, a mode indication section 3*d* which is lit when the auto-stop function is turned on, an electrode indication section 3*e* which indicates the ground electrode, and a position indication section 3*f* which shows the auto-stop setting position. Since the indication panel 3 has a relatively wide area as described above, it can indicate all data required for a root canal length measurement unit.

Figure 9:
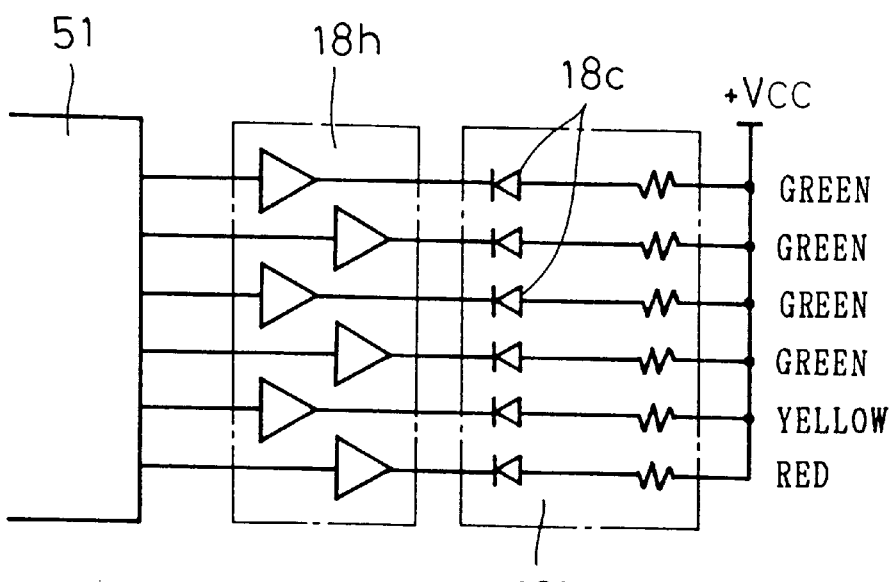
FIG. 9 is a circuit diagram of the indication means of the handpiece of the embodiment.

Unlike this indication section 3, the indication section provided on the root canal length measurement module 18 of the handpiece 11 is composed of a plurality of LEDs 18*c* arranged in a row on the indication board 18*b*. The contents of the indication are thus limited. FIG. 9 shows an example of the circuit configuration of the indication board 18*b*. More specifically, six LEDs 18*c* are used in the example. The upper four LEDs are green, the next LED is yellow and the bottom LED is red. These LEDs are connected to the output ports of the CPU 51 via a buffer 18*h*. In the circuit shown in this figure, each LED 18*c* emits light when the level of its output port becomes low. To enhance its visibility, each LED is designed to flash by repeatedly setting its level to H and L. When indicating the result of root canal length measurement, that is, the insertion position of the cutting tool 15 by using the above-mentioned structure, the LEDs emit light sequentially beginning with the top one in accordance with the amount of insertion. As the tool is inserted further and comes close to a preset auto-stop position, more LEDs emit light and the yellow LED becomes to emit light. In the end, the red LED emits light to indicate that the tool has reached the auto-stop position. In the case of this indication, the red LED can emit light from the beginning to indicate the auto-stop position and then the LED can be made flashed when the cutting tool 15 has reached the position to indicate the condition. In this way, various information can be indicated depending on the presence or absence of flashing or by changing the period of flashing. Accordingly, this indication means having a simple structure only equipped with a plurality of light-emitting devices can separately indicate a certain amount of information by variously combining simple lighting mode, flashing mode, flashing period and color of light to be emitted. In addition to visual indication by using the above-mentioned light-emitting devices, an audio output such as an electronic buzzer sound and a synthesized voice sound can also be used for indication. This method is advantageous in that the operator can obtain information without moving his eyes from an affected part. A root canal length measurement unit which outputs information via an earphone is known. An audio output similar to this can be used for example. The indication means by this audio output can be installed either on the handpiece 11 or the charger 1. Since an electronic buzzer sound can be generated relatively easily, and a fairly large amount of information can be delivered by changing the kind, tone, intermittent period and intensity of sound, such a buzzer sound is one of appropriate indication means for the handpiece 11 which is require to be more lightweight.

Figure 10:
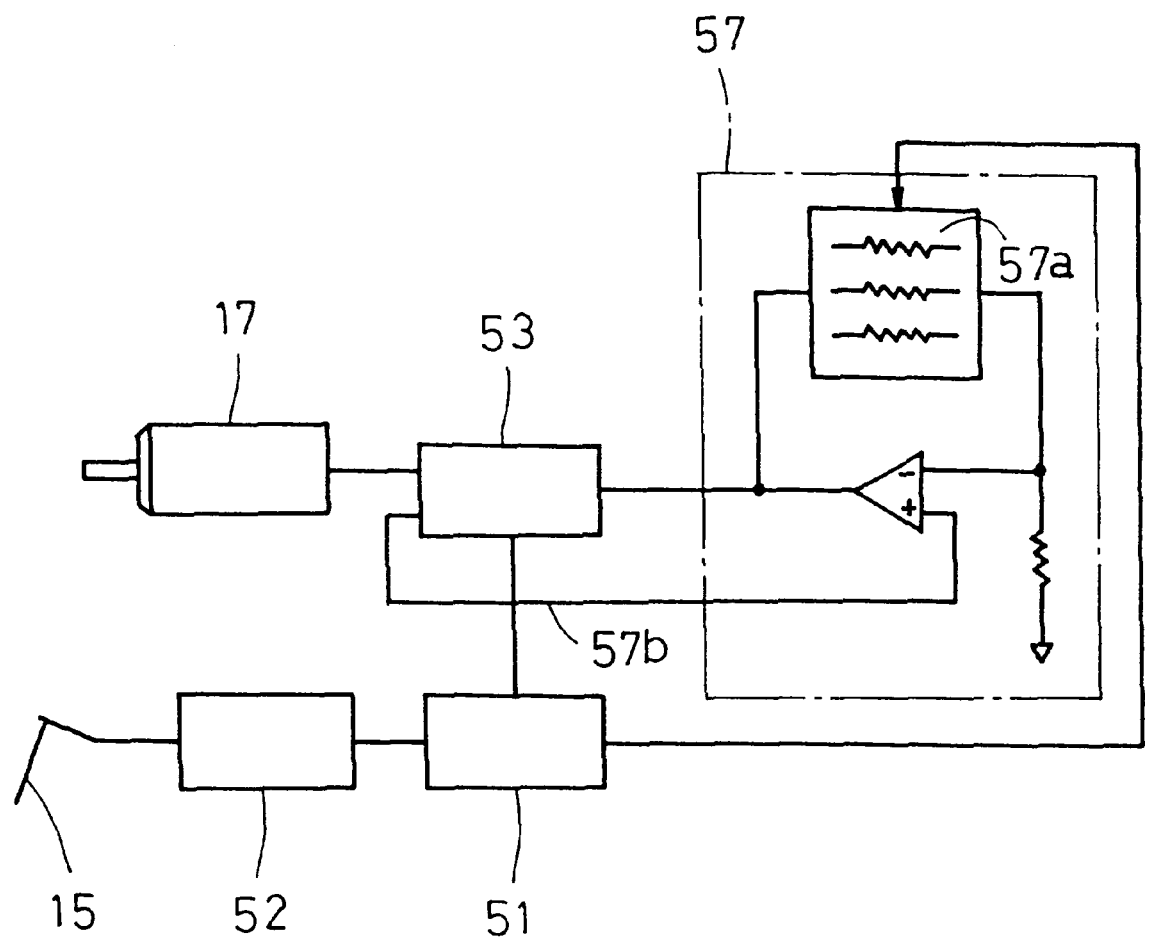
FIG. 10 is a block diagram of an improved control circuit of the embodiment.

By the way, since automatically stopping the rotation of the cutting tool or reducing the rotation speed thereof when the cutting tool has been inserted into a predetermined position in a root canal on the basis of the measurement results by the root canal length measurement circuit is known, such an operation is simply referred to as "auto-stop" in the above descriptions. Although one of the objects of the present invention is to improve the operability of the handpiece by making it cordless, the handpiece can have higher operability by improving the auto-stop control. FIG. 10 shows an example of a circuit for the auto-stop control. In this circuit, a feedback circuit 57 equipped with a gain adjuster 57*a* is provided. When a motor ON/OFF signal is output, the CPU 51 feeds back the motor drive output of a motor power supply section 53 to a feedback circuit 57 via a signal circuit 57*b* to adjust the motor drive output. The gain adjuster 57*a* is composed of an analog switch or the like for example. When the gain is maximized, the amount of feedback is maximized and the motor drive output becomes nearly zero. When the motor is turned on, the gain of the gain adjuster 57*a* is controlled by the CPU 51 so that the drive output of the motor power supply section 53 gradually rises until a value corresponding to a preset rotation speed is reached. The rotation speed of the motor 17 can thus be increased smoothly. Furthermore, when it is detected that the cutting tool 15 has become close to the setting position according to the data from the root canal length measurement circuit 52, the CPU 51 controls the gain of the gain adjuster 57*a* to gradually reduce the drive output of the motor power supply section 53. When the cutting tool 15 reaches the setting position, that is, a root apex, for example, the motor 17 is stopped completely. As a result, so-called slow-down control is performed and the root apex which is clinically important can be easily protected. In the case of a conventional handpiece, since the motor power supply is turned on and off by a relay, normal feedback is not activated. Therefore, there is a possibility that the motor causes an abnormality, that is, the motor rotates at high speed at the instant of turning on the motor power supply. In the case of the handpiece of the present invention, by the above-mentioned feedback and control actions, the motor 17 can be turned on and off smoothly without causing abnormal rotation and without giving a sense of confusion to the operator, thereby further improving the operability of the handpiece. When it is difficult to install the feedback circuit 57 on the control circuit board 18*a* of the handpiece 11 due to limitations of space, a control means for preventing any abnormality at the instant of turning on the motor power supply may be installed in the charger 1, and signals may be transmitted and received by a wire communication means.

Figure 11:
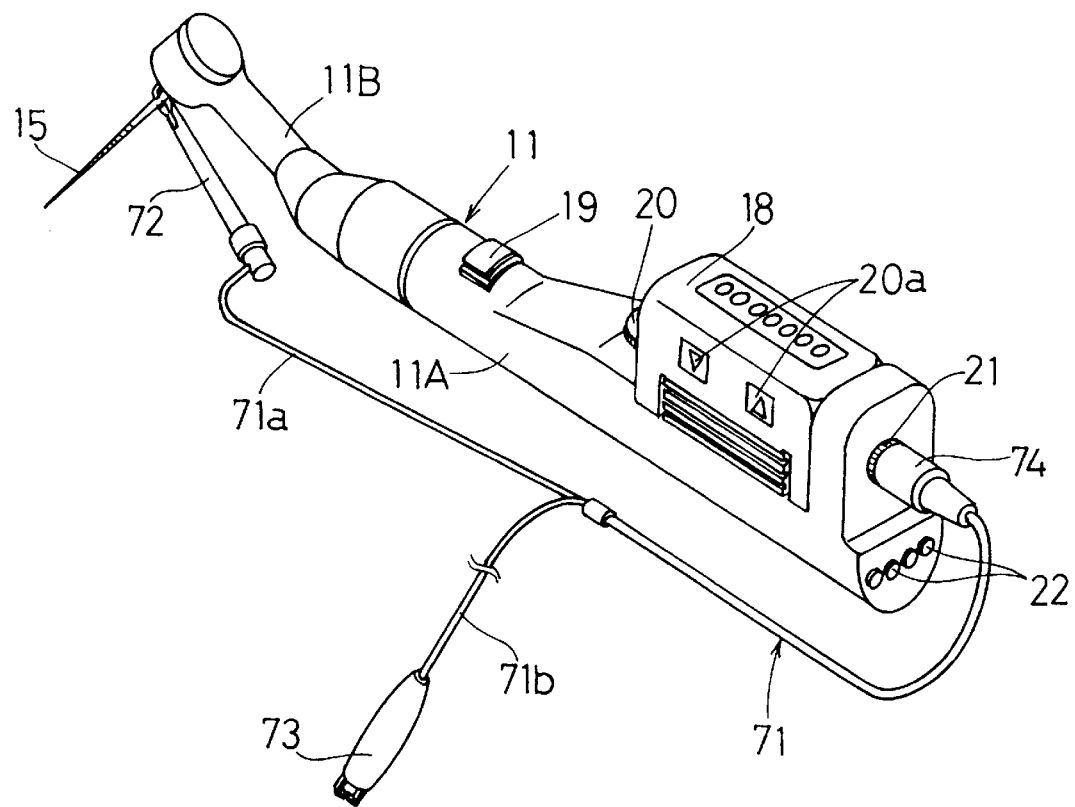
FIG. 11 is a perspective view of another embodiment of a handpiece.

In the above-mentioned embodiment, the terminal 18*e* of the root canal length measurement module 18 is made electrically conductive to the cutting tool 15 installed in the head 14 via the electrically conductive members in the main unit 11A and the head unit 11B. This conduction circuit can be made without passing all the internal members of the handpiece 11. For example, the internal members of at least the head 14 can be used for conduction and the remaining route can be replaced with an external lead wire extended along the handpiece 11. With this structure, the external lead wire does not cause much interference. As a result, the operability is not reduced and the internal structure of the handpiece 11 is relatively simplified. FIG. 11 shows a further simplified embodiment, wherein the conduction circuit to the cutting tool 15 is entirely formed by external lead wires. In the figure, numeral 71 represents an external lead wire comprising a measurement electrode lead wire 71a and a ground electrode lead wire 71b. Numeral 72 represents a measurement electrode, numeral 73 represents a ground electrode, and numeral 74 represents a connector. In this case, a two-pole type is used for the jack 21 for root canal length measurement. To this jack, the terminals 18e and 18f of the root canal length measurement module 18 are connected. During root canal length measurement, the connector 74 is connected to the jack 21 and the measurement electrode 72 is connected to the cutting tool 15 as shown in the figure. The lengths of the lead wires 71 and 71a to the cutting tool 15 should be as short as possible, and these lead wires should be placed close to the handpiece 11. With this arrangement, the external lead wire 71 does not cause much interference. In addition, the feature of the cordless handpiece, which does not require any external wires from the control unit to the cutting tool 15, can be retained. Therefore, the operability of this handpiece is better than that of the conventional handpiece.

Generally, in this kind of handpiece, the cutting tool which is also used as the electrode for root canal length measurement is very thin and apt to be broken easily when excessive force is applied thereto. The cutting tool can be prevented from being broken by detecting the drive power thereof and by automatically stopping or reversely rotating the cutting tool or reducing the operating speed thereof when the drive power exceeds a setting value. The operability of the handpiece can also be improved. In the following descriptions, the control for automatically stopping or reversely rotating the cutting tool or reducing the operating speed thereof when the drive power of the cutting tool exceeds a setting value is generally referred to as "overtorque stop." The motor current detection resistor 56 shown in FIG. 6 is provided for this overtorque stop control. In this embodiment, the drive power is detected depending on the amount of the current flowing the motor 17. More specifically, the voltage generated in the resistor 56 depending on the amount of the current is input to the CPU 51. When this value exceeds a setting value, control is performed so that the motor 17 is stopped or reversely rotated or the rotation speed is reduced. This control prevents the cutting tool 15 from being broken and can provide an easy-to-use handpiece. Although a dedicated setting control section can be provided as the control section for setting the above-mentioned setting value, the auto-stop position setting switch 5, the main switch 19 and the speed controller 20 and the foot pedal 8, for example, can also be used as this control section.

Figure 12:
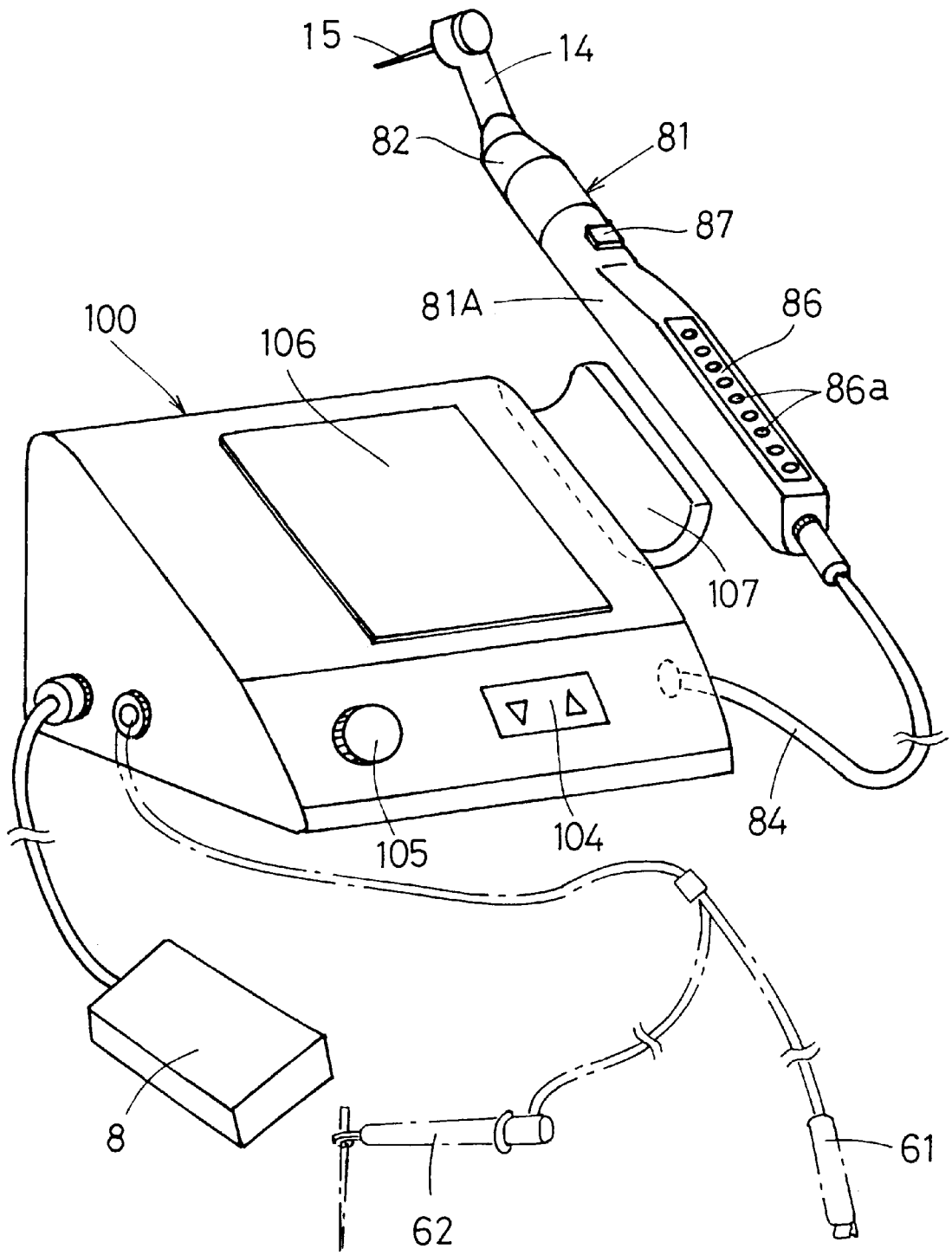
FIG. 12 is an external perspective view of an embodiment of an entire apparatus of the present invention, wherein the handpiece is connected to the main control unit via a tube.
Figure 13:
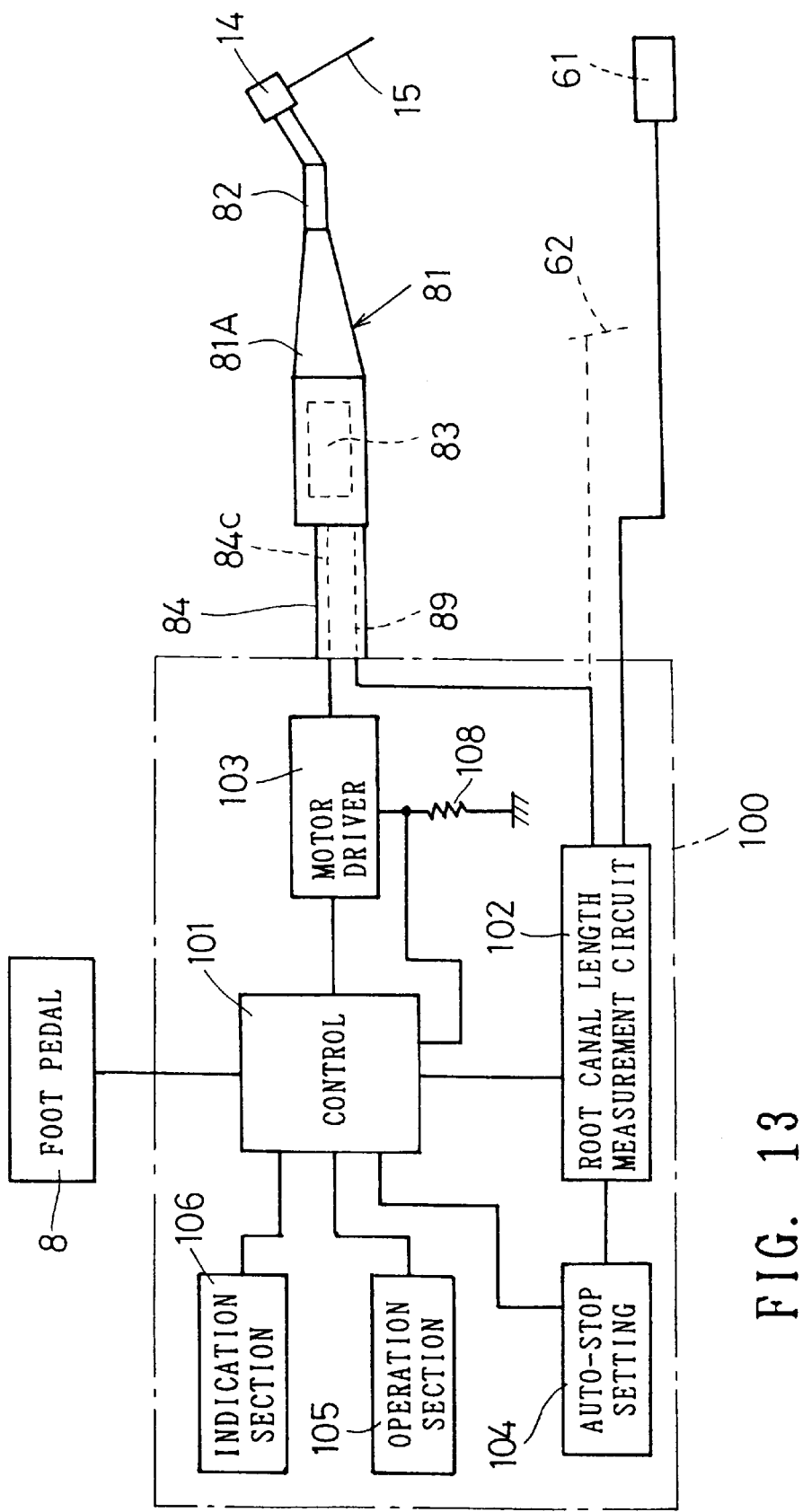
FIG. 13 is a block diagram of the embodiment.
Figure 14:
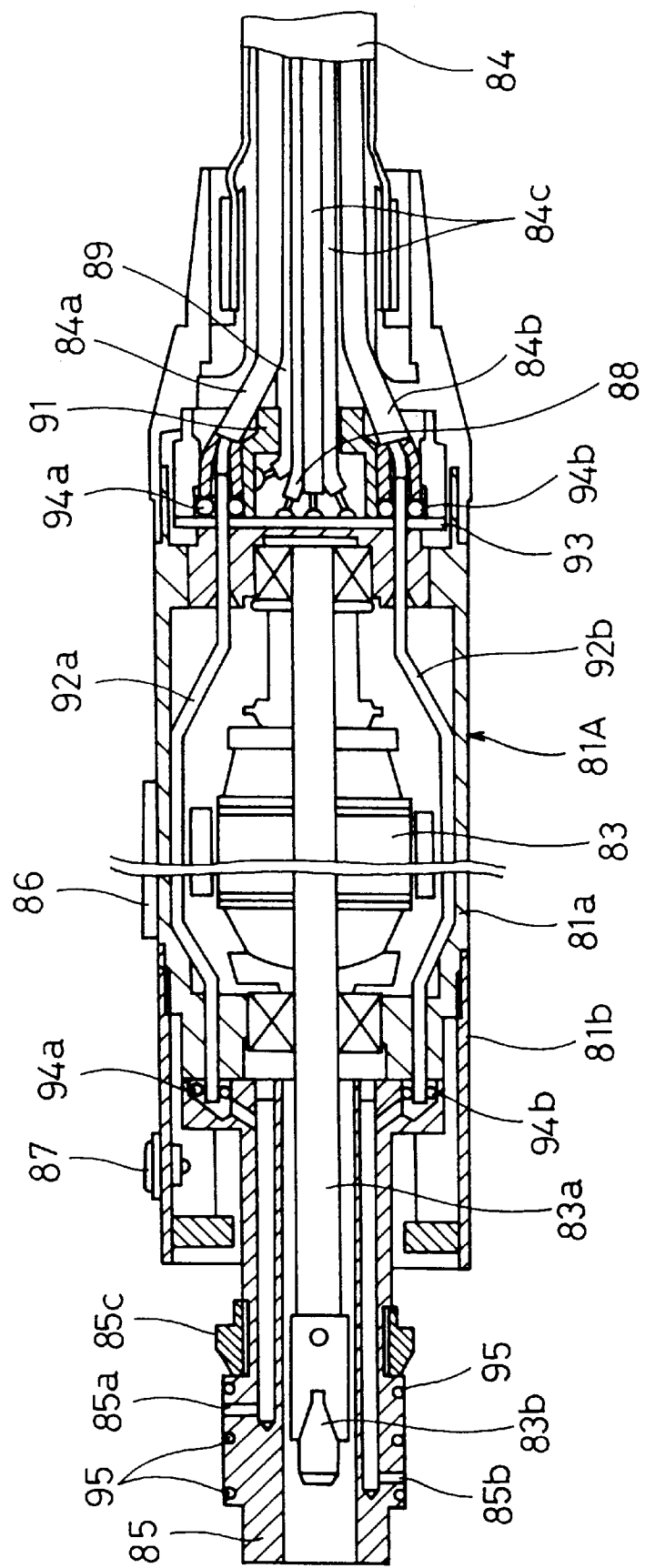
FIG. 14 is a sectional view of an embodiment of the main unit of the handpiece used for the above-mentioned apparatus.
Figure 15:
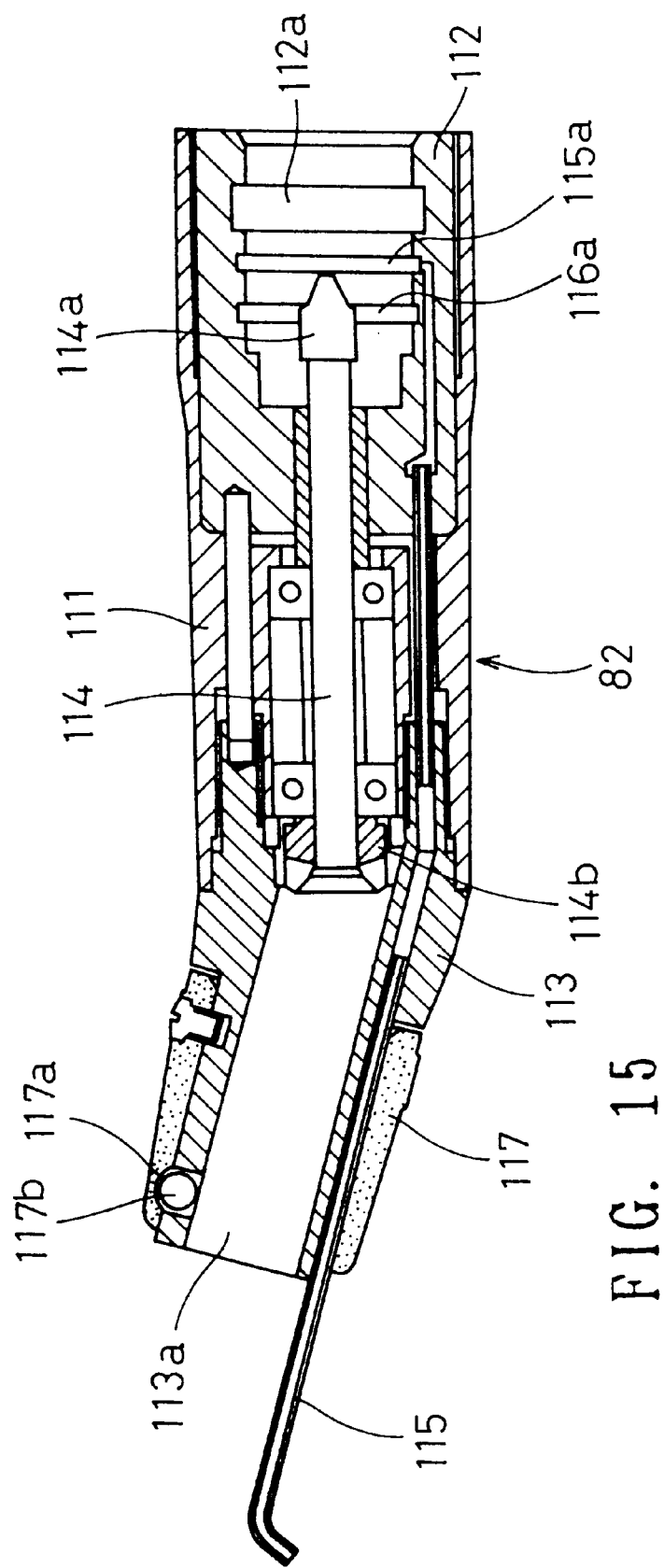
FIG. 15 is a sectional view of the shank section of the above-mentioned handpiece.
Figure 16:
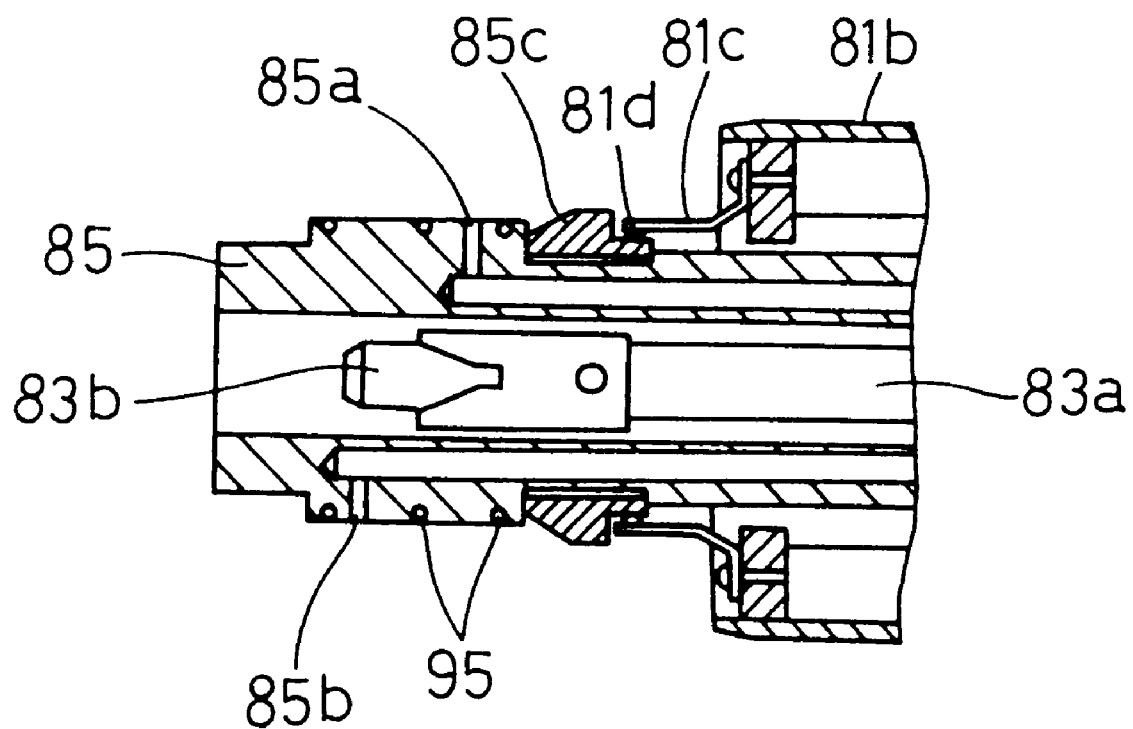
FIG. 16 is a sectional view of a main section of another embodiment of the main unit of the above-mentioned handpiece.

Auto-stop or overtorque stop described in the above-mentioned embodiments are not limitedly applied to a cordless handpiece, but they can be adopted to a conventional apparatus wherein the handpiece is connected to the main control unit via a tube. With this control, the operability of the apparatus can be improved. FIGS. 12 and 13 show an embodiment of a conventional apparatus, and FIGS. 14 to 16 show an embodiment of a handpiece used for the apparatus.

In FIGS. 12 and 13, numeral 81 represents a handpiece, numeral 100 represents a desk-top type of main control unit, the handpiece 81 comprises the head 14 having the structure shown in FIG. 4, a shank 82, etc. and is connected to the main control unit 100 via a tube 84. The main unit of the handpiece 81A has a built-in micromotor as a drive motor 83, and equipped with an indication section 86 and an operation switch 87. In FIG. 13, numeral 84c represents a motor lead wire, numeral 89 represents a signal lead wire for one of signal circuits of a root canal length measurement circuit 102. The indication section 86, the operation switch 87 and their control lead wires are not shown. The main control unit 100 has a control section 101, a root canal length measurement circuit 102, a motor driver 103, an auto-stop position setting section 104, an operation section 105, an indication section 106, a holder 107 and a motor current detection resistor 108, and designed to allow the foot pedal 8, the measurement electrode 62 and the mouth electrode 61 to be connected. The control section 101 is used to control the entire apparatus and its main section is composed of a microcomputer. The auto-stop position is set by the auto-stop position setting section 104. The operation section 105 is used to select control modes. More specifically, the operation section selects the ON/OFF mode of the auto-stop control, that is, the section selects whether the auto-stop control is performed or not. When the auto-stop control is in the ON mode, the operation section selects whether the cutting tool 15 is stopped automatically or rotated reversely, or the rotation speed thereof is reduced when the tool has reached a setting position. The ON/OFF operation and the setting of the rotation speed of the motor 83, and root canal length measurement are done by operating the foot pedal 8 after the above-mentioned settings and selections have been completed. During root canal length measurement, the cutting tool 15 installed in the head 14 is used as a measurement electrode, and this electrode and the mouth electrode are used as a set. A dedicated electrode can also be used as the measurement electrode 62 to perform root canal length measurement. An operation section conforming to any desired specifications can be provided for the foot pedal 8, although such an operation section is not shown in FIG. 12.

An example of standard usage is described above. However, the structure can be modified so that the settings and selections by the operation section 105 can also be done by the foot pedal 8. In addition, although the operation switch 87 installed on the main unit 81 A of the handpiece is not used in the above-mentioned example, the functions of the foot pedal 8 can be assigned to the operation switch 87, without using the foot pedal 8 at all. Or the functions of the operation section 105 can be assigned to the operation switch 87. In this way, it is not necessary to think that the functions of the operation section 105, the foot pedal 8 and the operation switch 87 are fixed. Therefore, the combinations of the functions can be selected in accordance with the specifications of the entire apparatus, and unnecessary functions can be omitted. The motor current detection resistor 108 shown in FIG. 13 is provided for overtorque stop control. The drive power of the motor 83 is detected indirectly by detecting the operation current of the motor driver 103. That is to say, the voltage generated across the resistor 108 depending on the current is detected by the control section 101. When the detected value exceeds a setting value, the motor 83 is stopped or rotated reversely or the rotation speed thereof is reduced. By this control, the cutting tool 15 can be prevented from being broken. The structure is formed so that the setting operation of the above-mentioned setting value can be done by the foot pedal 8, the auto-stop setting section 104 or the operation section 105, for example.

In the following descriptions, the handpiece 81 is described in detail. This handpiece 81 has a structure wherein the head 14 is set in the main unit 81A of the handpiece via the shank 82 and is equipped with water/air supply functions.

In FIGS. 14 and 15, numeral 81a represents a motor housing, and numeral 81b represents a cover. Inside the motor housing 81a, the motor 83 having a clutch 83b at the tip of the output shaft 83a thereof is built in. At one end, a connection tube 84 is provided to make connection between the end and the main control unit 100 (not shown in the figure). At the other end, that is, on the tip side, a head 85 in which a shank 82 is inserted is provided. In addition, the indication section 86 and the operation switch 87 are provided on the outer circumference section. As the indication section 86, a plurality of LEDs 86a for example are arranged to indicate information by the lighting or flashing of the LEDs.

The tube 84 is equipped with a water supply tube 84a, an air tube 84b, motor lead wires 84c and a control lead wire 88 for the indication section 86 and the operation switch 87. Furthermore, the tube is also equipped with a signal lead wire 89 electrically connected to one of signal circuits of the root canal length measurement circuit provided externally separate from the handpiece. The water supply tube 84a is connected to a joint 91, thereby leading to the opening section 85a of the outer circumference surface of the head 85 via a water pipe 92a. In a similar manner, the air tube 84b is connected to the joint 91, thereby leading to the opening section 85b of the outer circumference surface of the head 85 via an air pipe 92b. The signal lead wire 89 is also connected to the joint 91. Although no specific route is shown, the motor lead wires 84c are connected to the motor 83 via a terminal block 93, and the control lead wire 88 is connected to the indication section 86 and the operation switch 87. The above-mentioned joint 91, pipes 92a, 92b and the head 85 are made of metallic materials. The O-rings 94a, 94b provided at both ends of the pipes 92a, 92b, and the O-ring 95 mounted on the outer circumference of the head 85 are made of electrically conductive rubber. Therefore, the signal lead wire 89 is electrically connected to the head 85 via the joint 91, the O-rings 94a, 94b and the pipes 92a, 92b.

The shank 82 is composed of a housing 111 in which a connection cylinder 112 and a body 113 are assembled integrally. At the axial center section thereof, a drive shaft 114 is supported. At the one end of the drive shaft 114, a clutch 114a is provided, and at the other end, a drive gear 114b is provided. When the connection cylinder 112 is fit to the head 85 of the main unit 81A, the fixing spring ring 85c of the head 85 engages the ring groove 112a of the connection cylinder 112 to prevent disconnection. As a result, the cylinder 112 is rotatably connected to the main unit 81A. A water supply pipe 115 leads to the opening section 85a of the main unit 81A via a ring groove 115a. In a similar manner, an air pipe (not shown) provided parallel to the water supply pipe 115 leads to the opening section 85b of the main unit 81A via a circular groove 116a. The body 113 has a cylindrical insertion hole 113a. Outside the body 113, a ring member 117 having an eccentric groove 117a on the inner circumference surface thereof is provided. By rotating this ring member 117, a ball 117b is exposed to the insertion hole 113a. When the bearing holder 14b of the head 14 is inserted into an insertion hole 113a, the ball 117b engages a hole 27b provided on the outside surface. By this engagement, the head 14 is installed in the shank 82. In this condition, the drive gear 114b engages the drive gear 14a of the head 14.

In this structure, the housing 111, the connection cylinder 112 and the body 113 of the shank 82 are made of metallic materials. When the shank 82 provided with the head 14 is mounted to the head 85 of the main unit 81A, the bearing holder 14b of the head 14 is connected to the signal lead wire 89 of the main unit 81A via the shank 82. In the above-mentioned case, the contact between the head 85 of the main unit 81A and the connection cylinder 112 of the shank 82 is securely established by the O-ring 95 made of electrically conductive rubber. In the above-mentioned example, since the signal lead wire 89 is connected to the head 85 via the water pipe 92a and the air pipe 92b, the motor housing 81a and the cover 81b are not necessarily required to be made of metallic materials. This structure is just an example, and other structures can also be adopted.

FIG. 16 shows an embodiment of another structure. The motor housing 81a and the cover 81b are made of metallic materials. A contact plate 81c equipped with a contact 81d on a plate spring or a plurality of such contact plates are provided on the cover 81b and made contact with a fixing spring ring 85c. More specifically, the fixing spring ring 85c is made of a metallic material and makes contact with the body 113 of the shank 82 at sufficient contact pressure by the elasticity of the spring ring. Attention is given to this matter in this embodiment, and the ring 85c is used for preventing disconnection and for establishing electrical conduction. With this structure, the contact between the head 85 and the ring 85c, which is apt to be insufficient due to the structure, is assisted by the contact plate 81c, thereby making the conduction reliable and thus making stable measurement possible. The shape of the contact plate 81c is not limited to the shape shown in the figure, but other appropriate shapes can be adopted. Furthermore, without contacting the contact with the fixing spring ring 85c as described above, a structure wherein the contact can be directly made contact with the connection cylinder 112 of the shank 82 can also be used.

In the apparatus of the present invention, the head itself forms a part of the signal transmission circuit for root canal length measurement as shown in FIG. 4 and does not need lead wires to be connected externally. Next, other embodiments of such a head are described below referring to FIGS. 17 to 20.

Figure 17:
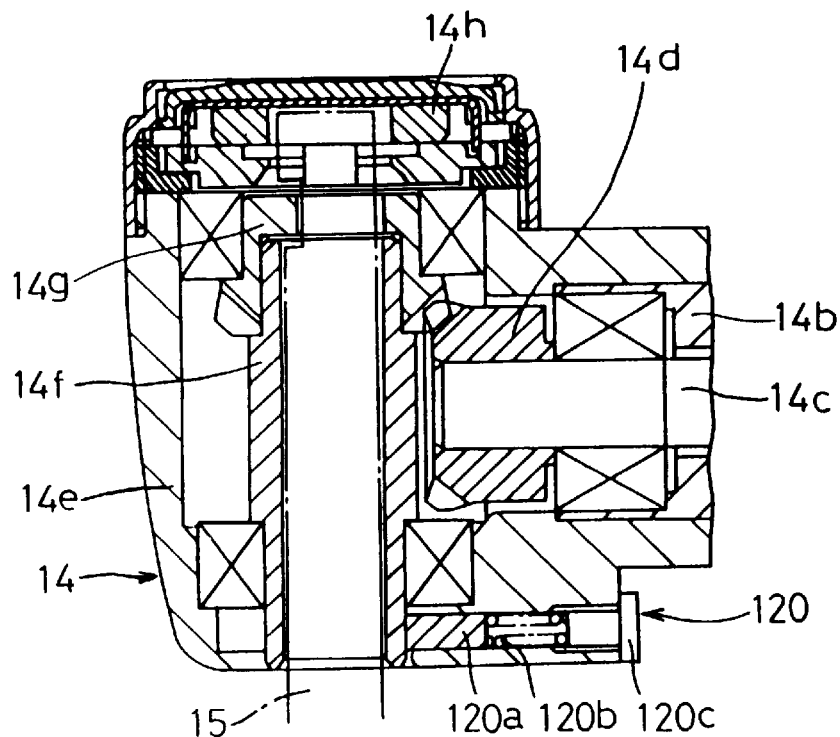
FIG. 17 is a sectional view of the main section of another embodiment of the head.

In FIG. 17, a signal transmission circuit is formed via a brush mechanism. A brush mechanism 120 comprising a brush 120a, a holding spring 120b and a stop screw 120c is installed in a head housing 14e, and the brush 120a is made contact with the outer circumference surface of a rotor 14f. In the embodiment shown in FIG. 4, the head housing 14e can be made of an insulating material such as a synthetic resin since the head housing 14e is not an essential part in the conduction circuit. In this embodiment, however, the head housing 14e is also made of an electrically conductive material such as a metallic material. By establishing conduction between the head housing 14e and the rotor shaft 14f using the brush mechanism 20, momentary disconnection in the conduction circuit, which may occur when a gear mechanism constitutes a part of the conduction circuit and the two gears of the gear mechanism are separated momentarily from each other during rotation, is prevented, and the conduction is made reliable and stable measurement can be performed easily.

Figure 18:
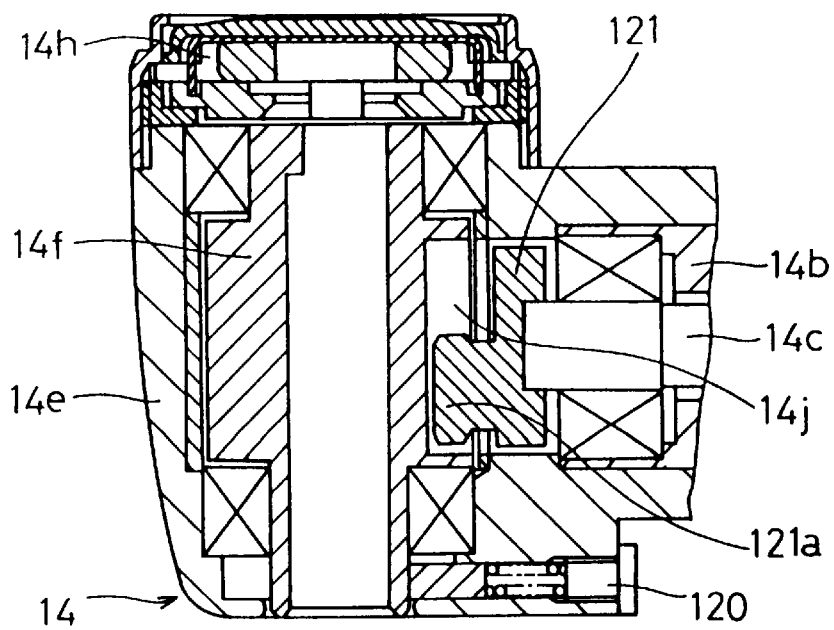
FIG. 18 is a sectional view of the main section of still another embodiment of the head.

FIG. 18 shows an embodiment of a head wherein a rotor shaft 14f is subjected to twist operation by a conversion mechanism which converts continuous rotation in the same direction into reciprocating rotation. More specifically, a slot 14j is formed on the outer circumference surface of the rotor shaft 14f in the axial direction. In accordance with this change, instead of a front gear, a drive member 121 equipped with an eccentric convex section 121a is fixed to the drive shaft 14c, and the convex section 121a engages the slot 14j. As a result, when the drive shaft 14c is rotated, the convex section 121a executes a circular motion. In accordance with the circular motion, the rotor shaft 14f repeats reciprocating rotation within a certain range. Also in this embodiment, electrical conduction is established between the head housing 14e and the rotor shaft 14f by the brush mechanism 120 in the manner similar to that shown in FIG. 17. As a result, conduction is retained and stable measurement can be done.

Figure 19:
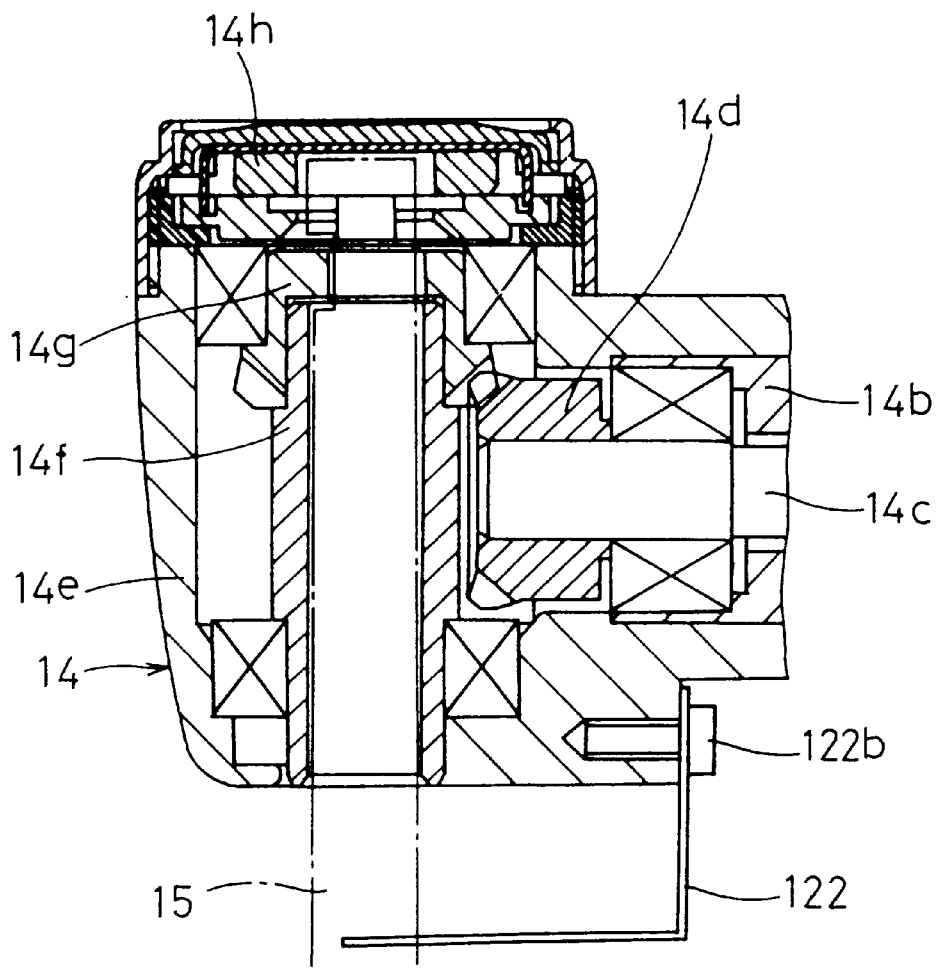
FIG. 19 is a sectional view of the main section of a still further embodiment of the head.
Figure 20:
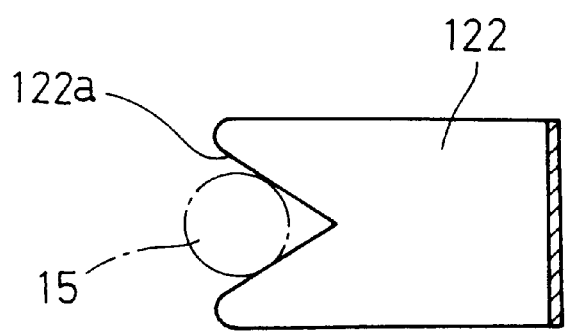
FIG. 20 is a plan view of the tip section of the contact piece of the above-mentioned head.

FIG. 19 shows a conduction circuit which is formed by bypassing the drive power transmission mechanism, unlike the above-mentioned embodiments. More specifically, numeral 122 represents a contact piece made of an electrically conductive plate material with high elasticity, such as phosphor bronze. The contact piece is fixed to the head housing 14e with a fixing screw 122b. As shown in FIG. 20, a V-shaped cutout section 122a is formed at the tip of the contact piece 122. The cutting tool 15 installed in the tool holding mechanism 14h is inserted into the cutout section 122a so that the contact piece 122 makes contact with the cutting tool 15 at a predetermined contact pressure. Also in this embodiment, the head housing 14e is made of an electrically conductive material such as a metallic material. With the above-mentioned structure, the conduction between the bearing holder 14b and the cutting tool 15 is established via the head housing 14e and the contact piece 122. Therefore, external wires are not necessary to connect the lead wire for the measurement circuit to the cutting tool 15. Since moving parts such as gears are bypassed, reliable conduction can be established. Other than the continuous rotation in the same direction, such as that obtained by the mechanism shown in FIG. 17 and the reciprocating rotation, such as that obtained by the mechanism shown in FIG. 18, a reciprocating motion in the axial direction can also be used for the operation of the cutting tool 15. Desired motions can thus be executed by known mechanisms.

In all the above-mentioned embodiments, an insulating film is formed on the outer surface of the tool holding mechanism 14h, and an insulating film is also formed on the outer surface of the head housing 14e. As a result, measurement can be performed without problems, even when the head 14 makes contact with tissues in the mouth or the like. Since very thin films can be used as these insulating films, they are not shown in FIGS. 17 to 19.

What is claimed is:

1. A cordless handpiece comprising a main unit equipped with at least a cutting tool drive rotary motor, a root canal length measurement circuit and a power supply battery, and a head equipped with a rotary cutting tool which is also used as a root canal length measurement electrode, wherein electrical connection is established between said cutting tool and one of the terminals of said root canal length measurement circuit via an external lead wire, and further comprising a drive control means for automatically performing at least one of stopping and reducing the operating speed of said cutting tool when said cutting tool has been inserted into a setting position in a root canal on the basis of measurement results obtained by said root canal measurement circuit.

2. A cordless handpiece comprising a main unit equipped with at least a cutting tool drive rotary motor, a root canal length measurement circuit and a power supply battery, and a head equipped with a rotary cutting tool which is also used as a root canal length measurement electrode, wherein electrical connection is established between said cutting tool and one of the terminals of said root canal length measurement circuit via an external lead wire, and further comprising a drive control means for automatically reversely rotating said cutting tool when said cutting tool has been inserted into a setting position in a root canal on the basis of measurement results obtained by said root canal measurement circuit.

3. A cordless handpiece according to claim 2, wherein said handpiece is provided with a means for detecting the drive power of said cutting tool, and a drive control means for automatically reversely rotating said cutting tool when the detected drive power exceeds a preset value.

4. A cordless handpiece according to claim 1 or 2, which is provided with a setting means for setting said setting position.

5. A cordless handpiece according to claim 1 or 2, wherein said external lead wire can be connected and disconnected as desired.

6. A cordless handpiece according to claim 1 or 2, wherein at least a portion of the outer surface of said handpiece corresponding to a range of insertion into the mouth of a patient is made of an insulating material.

7. A cordless handpiece according to claim 1 or 2, wherein said handpiece is provided with a data indication means for indicating at least measurement results obtained by said root canal length measurement circuit or said setting position data set by said setting means.

8. A cordless handpiece according to claim 7, wherein said indication means is composed of a plurality of indication dots, and a flashing period and/or indication color of each indication dot are changed in accordance with the measurement results obtained by said root canal length measurement circuit.

9. A cordless handpiece according to claim 7, wherein said indication means is a device generating an audio output in accordance with the measurement results obtained by said root canal length measurement circuit.

10. A cordless handpiece according to claim 7, wherein said main unit equipped with said indication means is rotatably connected to said head.

11. A cordless handpiece according to claim 10, wherein a rotation mechanism is provided between said head and said main unit to establish electrical connection and prevent disconnection.

12. A cordless handpiece according to claim 1, wherein said handpiece is provided with a means for detecting the drive power of said cutting tool, and a drive control means for automatically stopping or reducing the operating speed of said cutting tool when the detected drive power exceeds a preset value.

13. A dental treatment apparatus with a root canal length measurement function comprising a cordless handpiece equipped with at least a cutting tool drive rotary motor, a root canal length measurement circuit and a power supply battery, and a charger equipped with at least a charge circuit for charging said power supply battery, and further comprising a bidirectional communication means which performs data transmission and reception between said handpiece and said charger.

14. A dental treatment apparatus with a root canal length measurement function according to claim 13, wherein said bidirectional communication means comprises a wire communication means which can perform data transmission and reception via a signal circuit formed by mutual connection of said handpiece and said charger when said handpiece is set in said charger.

15. A dental treatment apparatus with a root canal length measurement function according to claim 14, wherein said charger has a plurality of handpiece setting sections for charging said power supply batteries so that battery charging and data communication can be performed for a plurality of handpieces.

16. A dental treatment apparatus with a root canal length measurement function according to claim 13, wherein said bidirectional communication means comprises a wireless communication means which performs data transmission and reception when said handpiece is not set in said charger.

17. A dental treatment apparatus with a root canal length measurement function, wherein the main unit of a handpiece provided with a head equipped with a rotary cutting tool which is also used as a root canal length measurement electrode is connected to a separate main control unit via a tube, and said apparatus is provided with a drive control means for automatically stopping or reducing the operating speed of said cutting tool when said cutting tool has been inserted into a setting position in a root canal on the basis of the measurement results.

18. A dental treatment apparatus with a root canal length measurement function according to claim 17, which is provided with a means for detecting the drive power of said cutting tool, and a drive control means for automatically stopping or reducing the operating speed of said cutting tool when the detected drive power exceeds a preset value.

19. A dental treatment apparatus with a root canal length measurement function, wherein the main unit of a handpiece provided with a head equipped with a rotary cutting tool which is also used as a root canal length measurement electrode is connected to a separate main control unit via a tube, and said apparatus is provided with a drive control means for automatically reversely rotating said cutting tool when said cutting tool has been inserted into a setting position in a root canal on the basis of the measurement results.

20. A dental treatment apparatus with a root canal length measurement function according to claim 19, which is provided with a means for detecting the drive power of said cutting tool, and a drive control means for automatically reversely rotating said cutting tool when the detected drive power exceeds a preset value.

* * * * *